(12) United States Patent
Bhamidipati et al.

(10) Patent No.: US 7,713,987 B2
(45) Date of Patent: *May 11, 2010

(54) PYRIMIDINE-2,4-DIAMINES AND THEIR USES

(75) Inventors: Somasekhar Bhamidipati, Foster City, CA (US); Rajinder Singh, Belmont, CA (US)

(73) Assignee: Rigel Pharmaceuticals, Inc., South San Francisco, CA (US)

( * ) Notice: Subject to any disclaimer, the term of this patent is extended or adjusted under 35 U.S.C. 154(b) by 1118 days.

This patent is subject to a terminal disclaimer.

(21) Appl. No.: 11/295,752

(22) Filed: Dec. 6, 2005

(65) Prior Publication Data

US 2007/0129362 A1    Jun. 7, 2007

(51) Int. Cl.
C07D 403/12  (2006.01)
C07D 403/14  (2006.01)
C07D 413/14  (2006.01)
C07D 417/14  (2006.01)
A61K 31/506  (2006.01)
A61P 19/02   (2006.01)
A61P 35/00   (2006.01)

(52) U.S. Cl. ................. 514/275; 514/231.5; 514/224.2; 544/324; 544/48; 544/51; 544/105

(58) Field of Classification Search ................. 544/323, 544/324, 48, 51, 105; 514/275, 231.5, 224.2
See application file for complete search history.

(56) References Cited

U.S. PATENT DOCUMENTS

| | | | |
|---|---|---|---|
| 5,958,935 A | 9/1999 | Davis et al. | |
| 6,080,858 A | 6/2000 | Schumacher | |
| 6,878,687 B1 | 4/2005 | Ruben et al. | |
| 7,060,827 B2 | 6/2006 | Singh et al. | |
| 7,122,542 B2 | 10/2006 | Singh et al. | |
| 7,329,671 B2 | 2/2008 | Singh et al. | |
| 7,538,108 B2 * | 5/2009 | Singh et al. | 514/230.5 |
| 2004/0029902 A1 | 2/2004 | Singh et al. | |
| 2005/0209230 A1 | 9/2005 | Singh et al. | |
| 2005/0234049 A1 | 10/2005 | Singh et al. | |
| 2006/0058525 A1 | 3/2006 | Singh et al. | |
| 2006/0135543 A1 | 6/2006 | Singh et al. | |
| 2006/0167254 A1 | 7/2006 | Cooper et al. | |
| 2006/0211657 A1 | 9/2006 | Singh et al. | |
| 2006/0234983 A1 | 10/2006 | Singh et al. | |
| 2006/0270694 A1 | 11/2006 | Wong | |
| 2006/0293311 A1 | 12/2006 | Li et al. | |
| 2007/0004626 A1 | 1/2007 | Masuda et al. | |
| 2007/0060603 A1 | 3/2007 | Singh et al. | |
| 2007/0117775 A1 | 5/2007 | Payan | |
| 2007/0129360 A1 | 6/2007 | Phamidipati et al. | |
| 2007/0167439 A1 | 7/2007 | Singh et al. | |
| 2007/0197782 A1 | 8/2007 | Clough et al. | |
| 2007/0203161 A1 | 8/2007 | Argade et al. | |
| 2007/0203162 A1 | 8/2007 | Li et al. | |
| 2007/0225321 A1 | 9/2007 | Singh et al. | |
| 2007/0225495 A1 | 9/2007 | Singh et al. | |
| 2007/0293520 A1 | 12/2007 | Singh et al. | |
| 2007/0293521 A1 | 12/2007 | Singh et al. | |
| 2007/0293522 A1 | 12/2007 | Singh et al. | |
| 2007/0293523 A1 | 12/2007 | Singh et al. | |
| 2007/0293524 A1 | 12/2007 | Singh et al. | |
| 2007/0299095 A1 | 12/2007 | Singh et al. | |
| 2008/0221089 A1 | 9/2008 | Argade et al. | |

FOREIGN PATENT DOCUMENTS

| | | |
|---|---|---|
| WO | WO 00/39101 A1 | 7/2000 |
| WO | WO 00/59892 A1 | 10/2000 |
| WO | WO 01/00213 A1 | 1/2001 |
| WO | WO 01/19825 A1 | 3/2001 |
| WO | WO 01/29009 A1 | 4/2001 |
| WO | WO 01/40218 A1 | 6/2001 |
| WO | WO 01/47921 A1 | 7/2001 |
| WO | WO 01/72717 A1 | 10/2001 |
| WO | WO 01/72745 A1 | 10/2001 |
| WO | WO 02/22601 A1 | 3/2002 |
| WO | WO 02/46170 A2 | 6/2002 |
| WO | WO 02/46171 A2 | 6/2002 |
| WO | WO 02/46184 A1 | 6/2002 |
| WO | WO 02/47690 A1 | 6/2002 |
| WO | WO 03/063794 A2 | 8/2003 |
| WO | WO 2004/014382 A1 | 2/2004 |
| WO | WO 2005/009978 | 2/2005 |
| WO | WO 2005/016893 A2 | 2/2005 |

OTHER PUBLICATIONS

West, Anthony R., Solid State Chemistry and its Applications, Wiley, New York, 1988, pp. 358 & 365.*
Vippagunta et al., Advanced Drug Delivery Reviews 48: 3-26, 2001.*
Wolff Manfred E. "Burger's Medicinal Chemistry, 5ed, Part 1", John Wiley & Sons, 1995, pp. 975-977.*
Banker, G.S. et al, "Modern Pharmaceutices, 3ed.", Marcel Dekker, New York. 1996, pp. 451 and 596.*
Cha et al., Journal of Pharmacology and Experimental Therapeutics, 317(2), 571-578, 2006.*

(Continued)

Primary Examiner—Venkataraman Balasubramanian
(74) Attorney, Agent, or Firm—McDonnell Boehnen Hulbert & Berghoff LLP

(57) ABSTRACT

The present invention relates to diaryl pyrimidine-2,4-diamines, pharmaceutical compositions thereof, and the use of the compounds and compositions for the inhibition of kinases. The compounds, analogs, and pharmaceutically acceptable salts thereof, and pharmaceutical compositions can be used in the treatment and prevention of cancer.

36 Claims, 1 Drawing Sheet

OTHER PUBLICATIONS

Braselmann et al., Journal of Pharmacology and Experimental Therapeutics, 319(3), 998-1008, 2006.*

Mass, R. D., Int. J. Radiation Oncology Bio. Phys.vol. 58(3): 932-940, 2004.*

Fabbro et al. Pharmacology & therapeutics 93, 79-98, 2002.*

Cecil Textbook of Medicine, edited by Bennet, J.C., and Plum F., 20th edition,vol. 1, 1004-1010, 1996.*

Mocsai, A. et al., "Syk is Required for Integrin Signaling in Neutrophils," Immunity, Apr. 2002, pp. 547-558, vol. 16.

Sada, K. et al., "Structure and Function of Syk Protein-Tyrosine Kinase," J. Biochem., 2001, pp. 177-186, No. 130.

Turner, M. et al., "Tyrosine Kinase SYK: Essential Functions for Immunoreceptor Signalling," Immunology Today, Mar. 2000, pp. 148-154, vol. 21, No. 3.

Atwell et al. (2004) "A novel mode of Gleevec binding is revealed by the structure of spleen tyrosine kinase" J. Biol. Chem. 279(53):55827-55832; Electronically published Oct. 26, 2004.

U.S. Appl. No. 11/539,142, filed Oct. 5, 2006, Singh et al.
U.S. Appl. No. 11/782,581, filed Jul. 24, 2007, Singh et al.
U.S. Appl. No. 11/875,772, filed Oct. 19, 2007, Li et al.
U.S. Appl. No. 11/943,506, filed Nov. 20, 2007, Bhamidipati et al.
U.S. Appl. No. 12/028,581, filed Feb. 8, 2008, Argade et al.
U.S. Appl. No. 12/030,031, filed Feb. 12, 2008, Li et al.
U.S. Appl. No. 12/053,382, filed Mar. 21, 2008, Atuegbu et al.
U.S. Appl. No. 12/053,438, filed Mar. 21, 2008, Li et al.
U.S. Appl. No. 12/175,441, filed Jul. 17, 2008, Singh et al.
U.S. Appl. No. 12/193,627, filed Aug. 18, 2008, Li et al.
U.S. Appl. No. 12/199,705, filed Aug. 27, 2008, Singh et al.
U.S. Appl. No. 12/268,235, filed Nov. 10, 2008, Singh et al.
U.S. Appl. No. 12/268,218, filed Nov. 10, 2008, Singh et al.
U.S. Appl. No. 12/273,357, filed Nov. 18, 2008, Singh et al.

* cited by examiner

PYRIMIDINE-2,4-DIAMINES AND THEIR USES

FIELD OF INVENTION

The invention relates to compounds containing the pyrimidine-2,4-diamine moiety, particularly diaryl pyrimidine-2,4-diamines, compositions comprising the compounds, and methods of using the compounds and compositions for the inhibition of kinases. The compounds and compositions are useful for treating or modulating disease in which kinases may be involved, symptoms of such disease, or the effect of other physiological events mediated by kinases.

BACKGROUND OF THE INVENTION

The protein kinases constitute a large family of structurally related enzymes that are responsible for the control of a wide variety of signal transduction processes within the cell. (Hardie and Hanks (1995) The Protein Kinase Facts Book, I and II, Academic Press, San Diego, Calif.). Protein kinases are thought to have evolved from a common ancestral gene due to the conservation of their structure and catalytic function. Almost all kinases contain a similar 250-300 amino acid catalytic domain. Protein kinases catalyze phosphorylation of the hydroxyl moiety of serine, threonine or tyrosine. Thus, the kinases may be categorized into families by the substrates they phosphorylate (e.g., protein-tyrosine, protein-serine/threonine, lipids, etc.), and sequence motifs generally corresponding to each of the kinase families have been identified.

The phosphorylation and dephosphorylation is an important post-translational control element in eukaryotic signal transduction. The phosphorylation state of a given protein can govern its enzyme activity, protein-protein binding interactions, and cellular distribution. Thus, protein kinases represent a large family of proteins which play a central role in the regulation of a wide variety of cellular processes, maintaining control over cellular function. A partial list of such kinases includes abl, AKT, bcr-abl, Blk, Brk, Btk, c-kit, c-met, c-src, CDK1, CDK2, CDK3, CDK4, CDK5, CDK6, CDK7, CDK8, CDK9, CDK10, cRaf1, CSFir, CSK, EGFR, ErbB2, ErbB3, ErbB4, Erk, Fak, fes, FGFR1, FGFR2, FGFR3, FGFR4, FGFR5, Fgr, flt-1, Fps, Frk, Fyn, Hck, IGF-1R, INS-R, Jak, KDR, Lck, Lyn, MEK, p38, PDGFR, PIK, PKC, PYK2, ron, Syk, Src, tie, tie2, TRK, Yes, and Zap70. Inhibition of the kinases has become an important therapeutic target.

Kinases regulate many different cell processes including, but not limited to, proliferation, differentiation, apoptosis, motility, transcription, translation and other signaling processes, by adding phosphate groups to target proteins. Phosphorylation of target proteins occurs in response to a variety of extracellular signals (hormones, neurotransmitters, growth and differentiation factors, etc.), cell cycle events, environmental or nutritional stresses, etc. The appropriate protein kinase functions in signaling pathways to activate or inactivate, for example, a metabolic enzyme, regulatory protein, receptor, cytoskeletal protein, ion channel or pump, or transcription factor. Uncontrolled signaling due to defective control of protein phosphorylation has been implicated in a number of diseases, including, for example, inflammation, cancer, allergy/asthma, disease and conditions of the immune system, disease and conditions of the central nervous system, and angiogenesis.

For example, the Src family is composed of ten highly homologous cytosolic kinases which are critical components in an array of cell signaling pathways ranging from lymphocyte activation to cell growth and proliferation. Constitutive activation of these enzymes can lead to oncogenic cell transformation, making them putative drug targets for cancer therapies. Because of their importance in the regulation of these fundamental cellular processes, many studies have focused on developing inhibitors for the Src family kinase. However, the potent inhibitors that have been discovered lack the high selectivity that would be required for probing the cellular inhibition of an individual target kinase. Conventional inhibitor screens have produced few if any molecules which can discriminate between the active sites of the various Src family kinases.

WO01/00213 describes substituted pyrimidines as Src kinase inhibitors. WO01/40218 describes arylamine derivatives for use as anti-telomerase agents. WO00/39101 describes substituted pyrimidines as anti-cancer agents. WO01/29009 describes substituted pyrimidines as kinase inhibitors, while WO00/39101, WO00/59892, and WO01/47921 describe amino substituted pyrimidines as kinase inhibitors. U.S. Pat. No. 6,080,858 describes a process for preparing substituted pyrimidines. WO01/19825 describes amino substituted pyrimidines as synthetic intermediates. WO01/72745 describes 4-heteroaryl-substituted pyrimidines as inhibitors of CDK's. WO01/72717 describes 4-amino-5-cyanopyrimidines as inhibitors of CDK's. WO02/22601 describes 4-(pyrazol-5-ylamino)-pyrimidines as kinase inhibitors. WO02/46184 describes 4-(4-pyrazolyl)-pyrimidines as kinase inhibitors. WO02/46170 and WO02/46171 describes 2-anilino-pyrimidines as inhibitors of JNK and IKK, respectively. WO02/47690 describes 4-arylamino-pyrimidines as kinase inhibitors.

Many of the active 2,4-pyrimidinediamine compounds are also potent inhibitors of the tyrosine kinase Syk kinase. Examples of such 2,4-pyrimidinediamine are described, for example, in U.S. application Ser. No. 10/355,543 filed Jan. 31, 2003 (US2004/0029902A1), international application Serial No. PCT/US03/03022 filed Jan. 31, 2003 (WO 03/063794), U.S. application Ser. No. 10/631,029 filed Jul. 29, 2003, international application Serial No. PCT/US03/24087 (WO2004/014382), U.S. application Ser. No. 10/903,263 filed Jul. 30, 2004 (US2005/0234049), and international application Serial No. PCT/US2004/24716 (WO2005/016893).

The development of selective protein kinase inhibitors that can block the disease pathologies and/or symptoms resulting from aberrant protein kinase activity has generated much interest. However, additional compounds for inhibition of kinases and treatment and prevention of diseases associated with them are needed.

SUMMARY OF THE INVENTION

The present invention provides prodrugs of pyrimidine-2,4-diamine compounds, compositions comprising the prodrugs, methods and intermediates useful for synthesizing the prodrugs and methods of using the prodrugs, including in the treatment and/or prevention of diseases mediated by kinases.

The compounds of the invention generally comprise a biologically active pyrimidine-2,4-diamine compound that is substituted at the nitrogen atom of one or more primary or secondary amine groups with a progroup $R^P$. The progroup generally includes a group or moiety that is metabolized under the conditions of use to yield the active pyrimidine-2,4-diamine drug, and is covalently attached to the drug via a carbamate, a thiocarbamate, a dithiocarbamate, a urea, or a thiourea linkage.

Virtually any known pyrimidine-2,4-diamine compound that has biological, and hence therapeutic, activity can be protected at an available primary or secondary amine of the parent drug molecule with one or more progroups $R^P$ as described herein. Suitable active pyrimidine-2,4-diamine compounds are described, for example, in U.S. application Ser. No. 10/355,543 filed Jan. 31, 2003 (US2004/0029902A1), international application Serial No. PCT/US03/03022 filed Jan. 31, 2003 (WO 03/063794), U.S. application Ser. No. 10/631,029 filed Jul. 29, 2003, international application Serial No. PCT/US03/24087 (WO2004/014382), U.S. application Ser. No. 10/903,263 filed July 30, (US2005/0234049), and international application Serial No. PCT/US2004/24716 (WO2005/016893). In such pyrimidine-2,4-diamine compounds, the progroup(s) can be attached to any available primary or secondary amine, including, for example, the N2 nitrogen atom of the 2,4-pyrimidinediamine moiety, the N4 nitrogen atom of the pyrimidine-2,4-diamine moiety, and/or a primary or secondary nitrogen atom included in a substituent on the pyrimidine-2,4-diamine compound.

The compounds of the invention are potent inhibitors of kinases. Accordingly, in still another aspect, the present invention provides methods of inhibiting kinases comprising contacting a kinase with an effective amount of a compound or composition of the invention effective for inhibition. The methods can be practiced either in vitro or in vivo, and can be used as a therapeutic approach towards the treatment and/or prevention of diseases such as treatment of neoplasia including cancer and metastasis, promoting apoptosis, and in the treatment and prevention of other diseases associated with protein kinases.

Compounds of the present invention are useful for, but not limited to, the prevention or treatment of cancer and related diseases. The compounds of the invention have kinase inhibitory activity, therefore, the compounds of the invention can be useful in therapy as antineoplasia agents. Compounds of the invention can be useful for the treatment of carcinomas, hematopoietic tumors, solid tumors, sarcomas, retinoblastoma, hematopoietic malignancies, including leukemias and lymphomas, tumor-induced pleural or pericardial effusions, and are also useful for promoting apoptosis.

The compounds of this invention can act as inhibitors of protein kinases, such as Syk, Src, ErbB, KDR, CDK-2, LCK, CDK-5, IKK, JNK3, and thus be effective in the treatment of diseases associated with these protein kinases.

In one aspect, the present invention provides compounds containing the pyrimidine-2,4-diamine moiety, particularly diaryl pyrimidine-2,4-diamine moiety, and compositions comprising the compounds. The compounds have the general structure shown below:

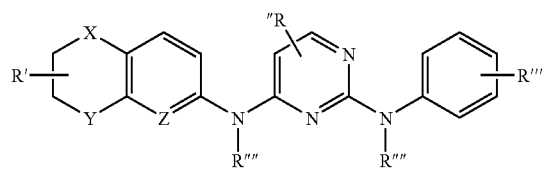

where X and Y are independently selected from oxygen, amino or substituted amino, $S(O)_{0-2}$, or substituted or unsubstituted carbon; R', R'', and R''' are optional substituents; and R'''' is H or a progroup, $R^P$. The progroup $R^P$ is covalently attached via a carbamate, a thiocarbamate, a dithiocarbamate, a urea, or a thiourea linkage to any one or more of the 2'-N, the 4'-N, or to X or Y when they are amino. The compounds and compositions can be used in methods for the inhibition of kinases.

In one aspect, the compounds of the invention have the formula (I):

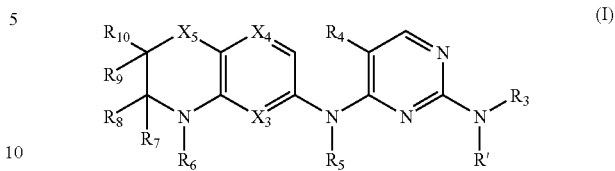

wherein $R_3$ is aryl or heteroaryl that is optionally substituted; $X_3$ and $X_4$ are independently selected from CH or N; $X_5$ is selected from the group consisting of $CR_{12}R_{13}$, O, S, SO, $SO_2$, and $NR_{14}$, wherein $R_{12}$ and $R_{13}$ are independently selected from H, OH, or lower alkyl; $R_4$ is an electronegative group; R', $R_5$, $R_6$ and $R_{14}$ are independently selected from H, lower alkyl, a progroup, cycloalkyl or aryl, and wherein at least one of R', $R_5$, $R_6$ or $R_{14}$ is the aforementioned progroup linked via a constituent carbamate, a thiocarbamate, a dithiocarbamate, a urea, or a thiourea linkage; $R_7$ and $R_8$ are independently selected from the group consisting of H, halogen, lower alkyl, cycloalkyl, aryl, and heteroaryl; $R_9$, and $R_{10}$ are independently selected from the group consisting of H, halogen, —OH, -alkoxy, lower alkyl, cycloalkyl, aryl, and heteroaryl; wherein $R_7$ and $R_8$, or $R_9$ and $R_{10}$ together form an oxo group, and provided $R_9$ or $R_{10}$ are not —OH or alkoxy when $X_5$ is $N_{14}$.

In another aspect, the present invention provides compounds of formula (II):

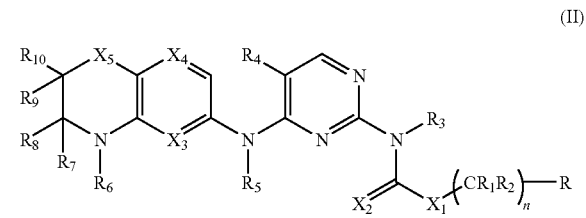

wherein $X_1$ is O, S, or $NR_{11}$; $X_2$ is selected from the group consisting of O and S; $X_3$ and $X_4$ are independently selected from CH or N; $X_5$ is selected from the group consisting of $CR_{12}R_{13}$, O, S, SO, $SO_2$, and $NR_{14}$ wherein $R_{12}$ and $R_{13}$ are independently selected from H, OH, lower alkyl, or together form an oxo; and $R_{14}$ is H or lower alkyl; R is selected from the group consisting of straight or branched, saturated or unsaturated alkyl, allyl, cycloalkyl, cycloalkyl, cycloheteroalkyl, aryl, heteroaryl, prenylalkaryl and heteroarylalkyl, each of which is optionally substituted; $R_1$ and $R_2$ are each independently selected from the group consisting of H, OH, —$OR_{11}$, $NR_{15}R_{15}$, halo, lower alkyl, —C(O)O-alkyl, —C(O)OH, —OP(=O)($OR_{11}$)$_2$, —OC(=O)$OR_{11}$, —OC(=O)$R_{11}$, cycloalkyl, aryl, heteroaryl or together form an oxo, wherein each $R_{15}$ is independently selected from H, lower alkyl, prenyl, allyl, —C(O)O-alkyl, cycloalkyl, aryl, heteroaryl, alkaryl and alkheteroaryl, or two of $R_{15}$ combine to form an optionally substituted cycloheteroalkyl; $R_3$ is aryl or heteroaryl, each optionally substituted; each $R_{11}$ is independently H or lower alkyl; $R_4$ is an electronegative group such as $NO_2$, fluorine, halogen, CN, haloalkyl, alkoxy, carboxylate, $CF_3$, $CHF_2$, $CH_2F$, $CF_3O$—, and the like; $R_5$ and $R_6$ are independently selected from H, lower alkyl, cycloalkyl or aryl; $R_7$, $R_8$, $R_9$, and $R_{10}$ are independently selected from the group consisting of H, OH, halogen, lower alkyl, cycloalkyl, aryl, and heteroaryl, or wherein $R_7$ and $R_8$ or $R_9$ and $R_{10}$ together form an oxo group; and n is an integer from 0 to 10.

In another aspect, the present invention provides methods of treating and/or preventing cancer. The methods generally involve administering to a subject that has cancer or that is at risk of developing cancer an amount of a compound or composition of the invention effective to treat or prevent the disease. The method may be practiced in animals or in humans.

Many of the active 2,4-pyrimidinediamine compounds are also potent inhibitors of the tyrosine kinase Syk kinase. Examples of such 2,4-pyrimidinediamine compounds are described, for example, in U.S. application Ser. No. 10/355,543 filed Jan. 31, 2003 (US2004/0029902A1), international application Serial No. PCT/US03/03022 filed Jan. 31, 2003 (WO 03/063794), U.S. application Ser. No. 10/631,029 filed Jul. 29, 2003, international application Serial No. PCT/US03/24087 (WO2004/014382), U.S. application Ser. No. 10/903,263 filed Jul. 30, 2004 (US2005/0234049), and international application Serial No. PCT/US2004/24716 (WO2005/016893). Thus, in still another aspect, the present disclosure provides methods of regulating, and in particular inhibiting, Syk kinase activity. The method generally involves contacting a Syk kinase or a cell comprising a Syk kinase with an amount of a suitable prodrug, or an acceptable salt, hydrate, solvate, N-oxide and/or composition thereof, effective to regulate or inhibit Syk kinase activity. In one embodiment, the Syk kinase is an isolated or recombinant Syk kinase. In another embodiment, the Syk kinase is an endogenous or recombinant Syk kinase expressed by a cell, for example a mast cell or a basophil cell. The method can be practiced in in vitro wherein the contacting is performed under conditions in which the progroup(s) metabolize to yield the active 2,4-pyrimidinediamine compound, or in in vivo for the treatment or prevention of diseases characterized by, caused by or associated with Syk kinase activity.

In another aspect, the present disclosure provides methods of regulating, and in particular inhibiting, signal transduction cascades in which Syk plays a role. The method generally involves contacting a Syk-dependent receptor or a cell expressing a Syk-dependent receptor with an amount of a suitable compound of the invention described herein, or an acceptable salt, hydrate, solvate, N-oxide and/or composition thereof, effective to regulate or inhibit the signal transduction cascade. The methods can also be used to regulate, and in particular inhibit, downstream processes or cellular responses elicited by activation of the particular Syk-dependent signal transduction cascade. The methods can be practiced to regulate any signal transduction cascade involving Syk.

DETAILED DESCRIPTION OF THE PREFERRED EMBODIMENTS

Definitions

Figure 1:
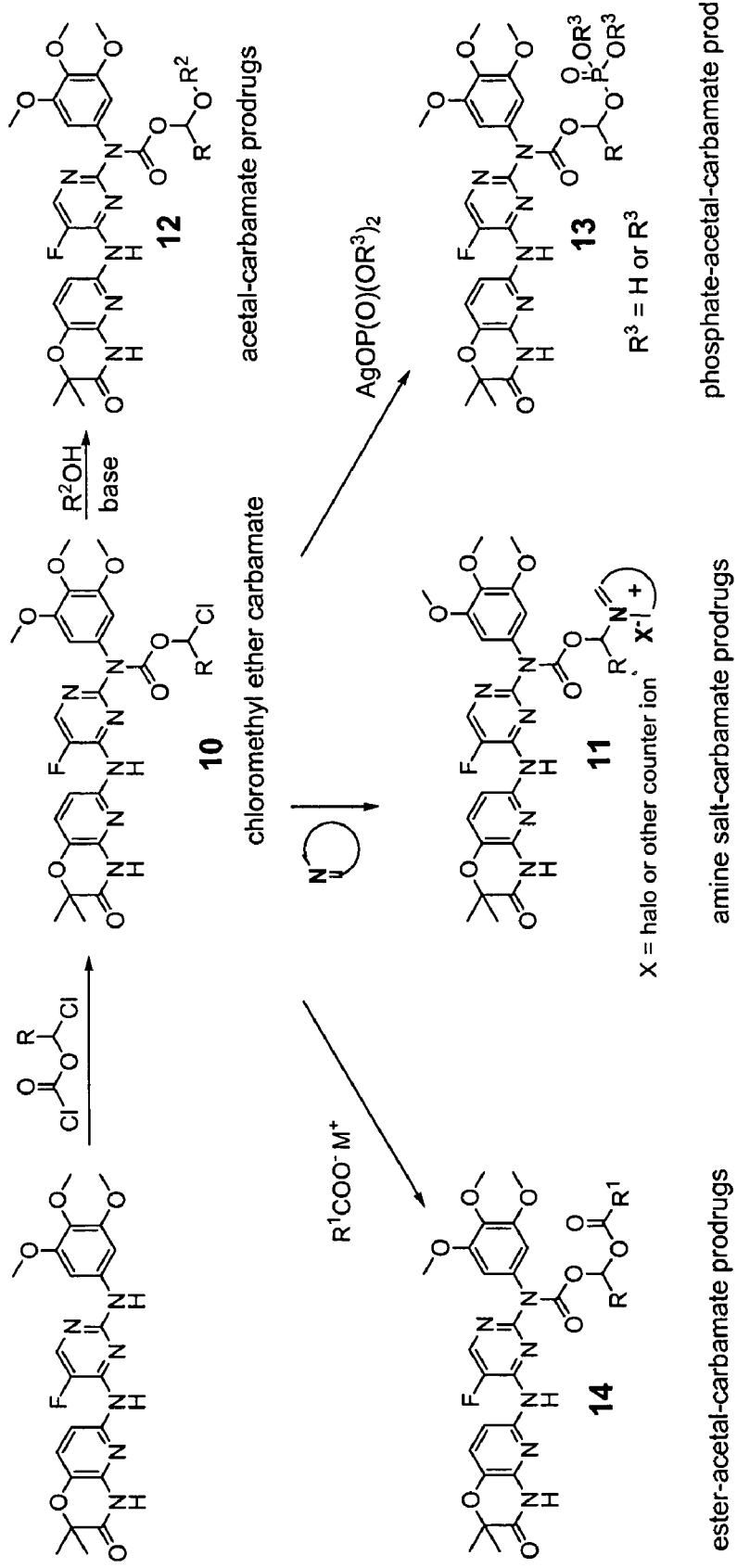
FIG. 1 illustrates carbamate-derived prodrugs of the pyrimidine-2,4-diamines.

Unless otherwise stated, the following terms used in this application, including the specification and claims, have the definitions given below. It must be noted that, as used in the specification and the appended claims, the singular forms "a," "an" and "the" include plural referents unless the context clearly dictates otherwise. Definition of standard chemistry terms may be found in reference works, including Carey and Sundberg (1992) "Advanced Organic Chemistry $3^{rd}$ Ed." Vols. A and B, Plenum Press, New York. The practice of the present invention will employ, unless otherwise indicated, conventional methods of mass spectroscopy, protein chemistry, biochemistry, recombinant DNA techniques and pharmacology, within the skill of the art.

As used herein, the following terms are intended to have the following meanings:

"Alkyl," by itself or as part of another substituent, refers to a saturated or unsaturated, branched, straight-chain or cyclic monovalent hydrocarbon radical derived by the removal of one hydrogen atom from a single carbon atom of a parent alkane, alkene or alkyne. Typical alkyl groups include, but are not limited to, methyl; ethyls such as ethanyl, ethenyl, ethynyl; propyls such as propan-1-yl, propan-2-yl, cyclopropan-1-yl, prop-1-en-1-yl, prop-1-en-2-yl, prop-2-en-1-yl(allyl), cycloprop-1-en-1-yl; cycloprop-2-en-1-yl, prop-1-yn-1-yl, prop-2-yn-1-yl, etc.; butyls such as butan-1-yl, butan-2-yl, 2-methyl-propan-1-yl, 2-methyl-propan-2-yl, cyclobutan-1-yl, but-1-en-1-yl, but-1-en-2-yl, 2-methyl-prop-1-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, but-1-yn-1-yl, but-1-yn-3-yl, but-3-yn-1-yl, etc.; and the like.

The term "alkyl" is specifically intended to include groups having any degree or level of saturation, i.e., groups having exclusively single carbon-carbon bonds, groups having one or more double carbon-carbon bonds, groups having one or more triple carbon-carbon bonds and groups having mixtures of single, double and triple carbon-carbon bonds. Where a specific level of saturation is intended, the expressions "alkanyl," "alkenyl," and "alkynyl" are used. Preferably, an alkyl group comprises from 1 to 15 carbon atoms ($C_1$-$C_{15}$ alkyl), more preferably from 1 to 10 carbon atoms ($C_1$-$C_{10}$ alkyl) and even more preferably from 1 to 6 carbon atoms ($C_1$-$C_6$ alkyl or lower alkyl).

"Alkanyl," by itself or as part of another substituent, refers to a saturated branched, straight-chain or cyclic alkyl radical derived by the removal of one hydrogen atom from a single carbon atom of a parent alkane. Typical alkanyl groups include, but are not limited to, methanyl; ethanyl; propanyls such as propan-1-yl, propan-2-yl(isopropyl), cyclopropan-1-yl, etc.; butanyls such as butan-1-yl, butan-2-yl(sec-butyl), 2-methyl-propan-1-yl(isobutyl), 2-methyl-propan-2-yl(t-butyl), cyclobutan-1-yl; pentanyls, such as pent-1-yl, pent-2-yl, pent-3-yl, cyclopent-1-yl; hexanyls, such as hexan-1-yl, hexan-3-yl, cyclohexan-1-yl, etc.; heptanyls, such as heptan-1-yl, heptan-2-yl, cycloheptan-1-yl, etc.; and the like.

"Alkenyl," by itself or as part of another substituent, refers to an unsaturated branched, straight-chain or cyclic alkyl radical having at least one carbon-carbon double bond derived by the removal of one hydrogen atom from a single carbon atom of a parent alkene. The group may be in either the cis or trans conformation about the double bond(s). Typical alkenyl groups include, but are not limited to, ethenyl; propenyls such as prop-1-en-1-yl, prop-1-en-2-yl, prop-2-en-1-yl(allyl), prop-2-en-2-yl, cycloprop-1-en-1-yl; cycloprop-2-en-1-yl; butenyls such as but-1-en-1-yl, but-1-en-2-yl, 2-methyl-prop-1-en-1-yl, but-2-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, etc.; and the like.

"Alkynyl," by itself or as part of another substituent refers to an unsaturated branched, straight-chain or cyclic alkyl radical having at least one carbon-carbon triple bond derived by the removal of one hydrogen atom from a single carbon atom of a parent alkyne. Typical alkynyl groups include, but are not limited to, ethynyl; propynyls such as prop-1-yn-1-yl, prop-2-yn-1-yl, etc.; butynyls such as but-1-yn-1-yl, but-1-yn-3-yl, but-3-yn-1-yl, etc.; and the like.

"Alkyldiyl" by itself or as part of another substituent refers to a saturated or unsaturated, branched, straight-chain or cyclic divalent hydrocarbon group derived by the removal of one hydrogen atom from each of two different carbon atoms of a parent alkane, alkene or alkyne, or by the removal of two hydrogen atoms from a single carbon atom of a parent alkane, alkene or alkyne. The two monovalent radical centers or each valency of the divalent radical center can form bonds with the same or different atoms. Typical alkyldiyl groups include, but are not limited to, methandiyl; ethyldiyls such as ethan-1,1-diyl, ethan-1,2-diyl, ethen-1,1-diyl, ethen-1,2-diyl; propyldiyls such as propan-1,1-diyl, propan-1,2-diyl, propan-2,2-diyl, propan-1,3-diyl, cyclopropan-1,1-diyl, cyclopropan-1,2-diyl, prop-1-en-1,1-diyl, prop-1-en-1,2-diyl, prop-2-en-1,2-diyl, prop-1-en-1,3-diyl, cycloprop-1-en-1,2-diyl, cycloprop-2-en-1,2-diyl, cycloprop-2-en-1,1-diyl, prop-1-yn-1,3-diyl, etc.; butyldiyls such as, butan-1,1-diyl, butan-1,2-diyl, butan-1,3-diyl, butan-1,4-diyl, butan-2,2-diyl, 2-methyl-propan-1,1-diyl, 2-methyl-propan-1,2-diyl, cyclobutan-1,1-diyl; cyclobutan-1,2-diyl, cyclobutan-1,3-diyl, but-1-en-1,1-diyl, but-1-en-1,2-diyl, but-1-en-1,3-diyl, but-1-en-1,4-diyl, 2-methyl-prop-1-en-1,1-diyl, 2-methanylidene-propan-1,1-diyl, buta-1,3-dien-1,1-diyl, buta-1,3-dien-1,2-diyl, buta-1,3-dien-1,3-diyl, buta-1,3-dien-1,4-diyl, cyclobut-1-en-1,2-diyl, cyclobut-1-en-1,3-diyl, cyclobut-2-en-1,2-diyl, cyclobuta-1,3-dien-1,2-diyl, cyclobuta-1,3-dien-1,3-diyl, but-1-yn-1,3-diyl, but-1-yn-1,4-diyl, buta-1,3-diyn-1,4-diyl, etc.; and the like. Where specific levels of saturation are intended, the nomenclature alkanyldiyl, alkenyldiyl and/or alkynyldiyl is used. Where it is specifically intended that the two valencies are on the same carbon atom, the nomenclature "alkylidene" is used. In preferred embodiments, the alkyldiyl group comprises from 1 to 6 carbon atoms (C1-C6 alkyldiyl). Also preferred are saturated acyclic alkanyldiyl groups in which the radical centers are at the terminal carbons, e.g., methandiyl(methano); ethan-1,2-diyl(ethano); propan-1,3-diyl(propano); butan-1,4-diyl (butano); and the like (also referred to as alkylenos, defined infra).

"Alkoxy," by itself or as part of another substituent, refers to a radical of the formula —OR, where R is an alkyl or cycloalkyl group as defined herein. Representative examples alkoxy groups include, but are not limited to, methoxy, ethoxy, propoxy, isopropoxy, butoxy, tert-butoxy, cyclopropyloxy, cyclopentyloxy, cyclohexyloxy and the like.

"Alkoxycarbonyl," by itself or as part of another substituent, refers to a radical of the formula —C(O)-alkoxy, where alkoxy is as defined herein.

"Alkylthio," by itself or as part of another substituent, refers to a radical of the formula —SR, where R is an alkyl or cycloalkyl group as defined herein. Representative examples of Alkylthio groups include, but are not limited to, methylthio, ethylthio, propylthio, isopropylthio, butylthio tert-butylthio, cyclopropylthio, cyclopentylthio, cyclohexylthio, and the like.

"Aryl," by itself or as part of another substituent, refers to a monovalent aromatic hydrocarbon group derived by the removal of one hydrogen atom from a single carbon atom of a parent aromatic ring system, as defined herein. Typical aryl groups include, but are not limited to, groups derived from aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene and the like. Preferably, an aryl group comprises from 6 to 20 carbon atoms ($C_6$-$C_{20}$ aryl), more preferably from 6 to 15 carbon atoms ($C_6$-$C_{15}$ aryl) and even more preferably from 6 to 10 carbon atoms ($C_6$-$C_{10}$ aryl).

"Arylalkyl," by itself or as part of another substituent, refers to an acyclic alkyl group in which one of the hydrogen atoms bonded to a carbon atom, typically a terminal or $sp^3$ carbon atom, is replaced with an aryl group as, as defined herein. Typical arylalkyl groups include, but are not limited to, benzyl, 2-phenylethan-1-yl, 2-phenylethen-1-yl, naphthylmethyl, 2-naphthylethan-1-yl, 2-naphthylethen-1-yl, naphthobenzyl, 2-naphthophenylethan-1-yl and the like. Where specific alkyl moieties are intended, the nomenclature arylalkanyl, arylalkenyl and/or arylalkynyl is used. Preferably, an arylalkyl group is ($C_6$-$C_{30}$) arylalkyl, e.g., the alkanyl, alkenyl or alkynyl moiety of the arylalkyl group is ($C_1$-$C_{10}$) alkyl and the aryl moiety is ($C_6$-$C_{20}$) aryl, more preferably, an arylalkyl group is ($C_6$-$C_{20}$) arylalkyl, e.g., the alkanyl, alkenyl or alkynyl moiety of the arylalkyl group is ($C_1$-$C_8$) alkyl and the aryl moiety is ($C_6$-$C_{12}$) aryl, and even more preferably, an arylalkyl group is ($C_6$-$C_{20}$) arylalkyl, e.g., the alkanyl, alkenyl or alkynyl moiety of the arylalkyl group is ($C_1$-$C_5$) alkyl and the aryl moiety is ($C_6$-$C_{10}$) aryl.

"Aryloxy," by itself or as part of another substituent, refers to a radical of the formula —O-aryl, where aryl is as defined herein.

"Arylalkyloxy," by itself or as part of another substituent, refers to a radical of the formula —O-arylalkyl, where arylalkyl is as defined herein.

"Aryloxycarbonyl," by itself or as part of another substituent, refers to a radical of the formula —C(O)—O-aryl, where aryl is as defined herein.

"Atropisomers" are stereoisomers resulting from hindered rotation about single bonds where the barrier to rotation is high enough to allow for the isolation of the conformers (Eliel, E. L.; Wilen, S. H. *Stereochemistry of Organic Compounds*; Wiley & Sons: New York, 1994; Chapter 14). Atropisomerism is significant because it introduces an element of chirality in the absence of stereogenic atoms. The invention is meant to encompass atropisomers.

"Carbamoyl," by itself or as part of another substituent, refers to a radical of the formula —C(O)NR'R", where R' and R" are each, independently of one another, selected from the group consisting of hydrogen, alkyl and cycloalkyl as defined herein, or alternatively, R' and R", taken together with the nitrogen atom to which they are bonded, form a 5-, 6- or 7-membered cycloheteroalkyl ring as defined herein, which may optionally include from 1 to 4 of the same or different additional heteroatoms selected from the group consisting of O, S and N.

"Compounds of the invention" refers to compounds encompassed by the various descriptions and structural formulae disclosed herein. The compounds of the invention may be identified by either their chemical structure and/or chemical name. When the chemical structure and chemical name conflict, the chemical structure is determinative of the identity of the compound. The compounds of the invention may contain one or more chiral centers and/or double bonds and therefore may exist as stereoisomers, such as double-bond isomers (i.e., geometric isomers), rotamers, enantiomers or diastereomers. Accordingly, when stereochemistry at chiral centers is not specified, the chemical structures depicted herein encompass all possible configurations at those chiral centers including the stereoisomerically pure form (e.g., geometrically pure, enantiomerically pure or diastereomerically pure) and enantiomeric and stereoisomeric mixtures. Enantiomeric and stereoisomeric mixtures can be resolved into their component enantiomers or stereoisomers using separation techniques or chiral synthesis techniques well known to the skilled artisan. The compounds of the invention may also exist in several tautomeric forms including the enol form, the keto form and mixtures thereof. Accordingly, the chemical structures depicted herein encompass all possible tautomeric forms of the illustrated compounds. The compounds of the invention may also include isotopically labeled compounds where one or more atoms have an atomic mass different from the atomic mass conventionally found in nature. Examples of isotopes that may be incorporated into the compounds of the invention include, but are not limited to, $^2$H, $^3$H, $^{11}$C, $^{13}$C, $^{14}$C, $^{15}$N, $^{18}$O, $^{17}$O, $^{31}$P, $^{32}$P, $^{35}$S, $^{18}$F and $^{36}$Cl. Compounds of the invention may exist in unsolvated forms as well as solvated forms, including hydrated forms and as N-oxides. In general, the hydrated, solvated and N-oxide forms are within the scope of the present invention. Certain compounds of the present invention may exist in multiple crystalline or amorphous forms. In general, all physical forms are equivalent for the uses contemplated by the present invention and are intended to be within the scope of the present invention.

"Cycloalkyl," by itself or as part of another substituent, refers to a saturated or unsaturated cyclic alkyl radical, as defined herein. Where a specific level of saturation is intended, the nomenclature "cycloalkanyl" or "cycloalkenyl" is used. Typical cycloalkyl groups include, but are not limited to, groups derived from cyclopropane, cyclobutane, cyclopentane, cyclohexane, cycloheptane, and the like. Preferably, the cycloalkyl group comprises from 3 to 10 ring atoms ($C_3$-$C_{10}$ cycloalkyl) and more preferably from 3 to 7 ring atoms ($C_3$-$C_7$ cycloalkyl).

"Cycloheteroalkyl," by itself or as part of another substituent, refers to a saturated or unsaturated cyclic alkyl radical in which one or more carbon atoms (and optionally any associated hydrogen atoms) are independently replaced with the same or different heteroatom. Typical heteroatoms to replace the carbon atom(s) include, but are not limited to, N, P, O, S, Si, etc. Where a specific level of saturation is intended, the nomenclature "cycloheteroalkanyl" or "cycloheteroalkenyl" is used. Typical cycloheteroalkyl groups include, but are not limited to, groups derived from epoxides, azirines, thiiranes, imidazolidine, morpholine, piperazine, piperidine, pyrazolidine, pyrrolidone, quinuclidine, and the like. Preferably, the cycloheteroalkyl group comprises from 3 to 10 ring atoms (3-10 membered cycloheteroalkyl) and more preferably from 5 to 7 ring atoms (5-7 membered cycloheteroalkyl).

A cycloheteroalkyl group may be substituted at a heteroatom, for example, a nitrogen atom, with a lower alkyl group. As specific examples, N-methyl-imidazolidinyl, N-methyl-morpholinyl, N-methyl-piperazinyl, N-methyl-piperidinyl, N-methyl-pyrazolidinyl and N-methyl-pyrrolidinyl are included within the definition of "cycloheteroalkyl." A cycloheteralkyl group may be attached to the remainder of the molecule via a ring carbon atom or a ring heteroatom.

"Dialkylamino" or "Monoalkylamino," by themselves or as part of other substituents, refer to radicals of the formula —NRR and —NHR, respectively, where each R is independently selected from the group consisting of alkyl and cycloalkyl, as defined herein. Representative examples of dialkylamino groups include, but are not limited to, dimethylamino, methylethylamino, di-(1-methylethyl)amino, (cyclohexyl)(methyl)amino, (cyclohexyl)(ethyl)amino, (cyclohexyl)(propyl)amino and the like. Representative examples of monalkylamino groups include, but are not limited to, methylamino, ethylamino, propylamino, isopropylamino, cyclohexylamino, and the like.

"Electronegative" by itself or as part of another substituent, refers to the tendency of a substituent to attract valence electrons from neighboring atoms. Exemplary electron-withdrawing groups include, acyl, formyl, sulfonyl, alkoxy, carboxylate, haloalkyl, chloride, fluoride, cyano, nitro, trifluoromethyl, difluoromethyl, fluoromethyl, trifluoromethoxy, difluoromethoxy, fluoromethoxy, MeO, and the like "Halogen" or "Halo," by themselves or as part of another substituent, refer to a fluoro, chloro, bromo and/or iodo radical.

"Haloalkyl," by itself or as part of another substituent, refers to an alkyl group as defined herein in which one or more of the hydrogen atoms is replaced with a halo group. The term "haloalkyl" is specifically meant to include monohaloalkyls, dihaloalkyls, trihaloalkyls, etc. up to perhaloalkyls. The halo groups substituting a haloalkyl can be the same, or they can be different. For example, the expression "($C_1$-$C_2$) haloalkyl" includes 1-fluoromethyl, 1-fluoro-2-chloroethyl, difluoromethyl, trifluoromethyl, 1-fluoroethyl, 1,1-difluoroethyl, 1,2-difluoroethyl, 1,1,1-trifluoroethyl, perfluoroethyl, etc.

"Haloalkyloxy," by itself or as part of another substituent, refers to a group of the formula —O-haloalkyl, where haloalkyl is as defined herein.

"Heteroalkyl," "Heteroalkanyl," "Heteroalkenyl," "Heteroalkynyl," "Heteroalkyldiyl" and "Heteroalkyleno," by themselves or as part of other substituents, refer to alkyl, alkanyl, alkenyl, alkynyl, alkyldiyl and alkyleno groups, respectively, in which one or more of the carbon atoms (and optionally any associated hydrogen atoms), are each, independently of one another, replaced with the same or different heteroatoms or heteroatomic groups. Typical heteroatoms or heteroatomic groups which can replace the carbon atoms include, but are not limited to, O, S, N, Si, —NH—, —S(O)—, —S(O)$_2$—, —S(O)NH—, —S(O)$_2$NH— and the like and combinations thereof. The heteroatoms or heteroatomic groups may be placed at any interior position of the alkyl, alkenyl or alkynyl groups. Examples of such heteroalkyl, heteroalkanyl, heteroalkenyl and/or heteroalkynyl groups include —CH$_2$—CH$_2$—O—CH$_3$, —CH$_2$—CH$_2$—NH—CH$_3$, —CH$_2$—CH$_2$—N(CH$_3$)—CH$_3$, —CH$_2$—S—CH$_2$, —CH$_3$, —CH$_2$—CH$_2$—S(O)—CH$_3$, —CH$_2$—CH$_2$—S(O)$_2$—CH$_3$, —CH=CH—O—CH$_3$, —CH$_2$—CH=N—O—CH$_3$, and —CH$_2$—CH$_2$—O—C≡CH. For heteroalkyldiyl and heteroalkyleno groups, the heteratom or heteratomic group can also occupy either or both chain termini. For such groups, no orientation of the group is implied.

"Heteroaryl," by itself or as part of another substituent, refers to a monovalent heteroaromatic radical derived by the removal of one hydrogen atom from a single atom of a parent heteroaromatic ring systems, as defined herein. Typical heteroaryl groups include, but are not limited to, groups derived from acridine, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like. Preferably, the heteroaryl group comprises from 5 to 20 ring atoms (5-20 membered heteroaryl), more preferably from 5 to 10 ring atoms (5-10 membered heteroaryl). Preferred heteroaryl groups are those derived from furan, thiophene, pyrrole, benzothiophene, benzofuran, benzimidazole, indole, pyridine, pyrazole, quinoline, imidazole, oxazole, isoxazole and pyrazine.

"Heteroarylalkyl" by itself or as part of another substituent refers to an acyclic alkyl group in which one of the hydrogen atoms bonded to a carbon atom, typically a terminal or $sp^3$ carbon atom, is replaced with a heteroaryl group. Where specific alkyl moieties are intended, the nomenclature heteroarylalkanyl, heteroarylakenyl and/or heteroarylalkynyl is used. In preferred embodiments, the heteroarylalkyl group is a 6-21 membered heteroarylalkyl, e.g., the alkanyl, alkenyl or alkynyl moiety of the heteroarylalkyl is (C1-C6) alkyl and the heteroaryl moiety is a 5-15-membered heteroaryl. In particularly preferred embodiments, the heteroarylalkyl is a 6-13 membered heteroarylalkyl, e.g., the alkanyl, alkenyl or alkynyl moiety is (C1-C3) alkyl and the heteroaryl moiety is a 5-10 membered heteroaryl.

"Parent Aromatic Ring System" refers to an unsaturated cyclic or polycyclic ring system having a conjugated π electron system. Specifically included within the definition of "parent aromatic ring system" are fused ring systems in which one or more of the rings are aromatic and one or more of the rings are saturated or unsaturated, such as, for example, fluorene, indane, indene, phenalene, etc. Typical parent aromatic ring systems include, but are not limited to, aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene and the like.

"Parent Heteroaromatic Ring System" refers to a parent aromatic ring system in which one or more carbon atoms (and optionally any associated hydrogen atoms) are each independently replaced with the same or different heteroatom. Typical heteroatoms to replace the carbon atoms include, but are not limited to, N, P, O, S, Si, etc. Specifically included within the definition of "parent heteroaromatic ring system" are fused ring systems in which one or more of the rings are aromatic and one or more of the rings are saturated or unsaturated, such as, for example, benzodioxan, benzofuran, chromane, chromene, indole, indoline, xanthene, etc. Typical parent heteroaromatic ring systems include, but are not limited to, arsindole, carbazole, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene and the like.

"Pharmaceutically acceptable salt" refers to a salt of a compound of the invention which is made with counterions understood in the art to be generally acceptable for pharmaceutical uses and which possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid and the like; or (2) salts formed when an acidic proton present in the parent compound is replaced by a metal ion, e.g., an alkali metal ion, an alkaline earth ion, or an aluminum ion; or coordinates with an organic base such as ethanolamine, diethanolamine, triethanolamine, N-methylglucamine, morpholine, piperidine, dimethylamine, diethylamine and the like. Also included are salts of amino acids such as arginates and the like, and salts of organic acids like glucurmic or galactunoric acids and the like (see, e.g., Berge et al., 1977, *J. Pharm. Sci.* 66:1-19).

"Pharmaceutically acceptable vehicle" refers to a diluent, adjuvant, excipient or carrier with which a compound of the invention is administered.

"Protecting group" refers to a group of atoms that, when attached to a reactive functional group in a molecule, mask, reduce or prevent the reactivity of the functional group. Typically, a protecting group may be selectively removed as desired during the course of a synthesis. Examples of protecting groups can be found in Greene and Wuts, *Protective Groups in Organic Chemistry*, $3^{rd}$ Ed., 1999, John Wiley & Sons, NY and Harrison et al., *Compendium of Synthetic Organic Methods*, Vols. 1-8, 1971-1996, John Wiley & Sons, NY. Representative amino protecting groups include, but are not limited to, formyl, acetyl, trifluoroacetyl, benzyl, benzyloxycarbonyl ("CBZ"), tert-butoxycarbonyl ("Boc"), trimethylsilyl ("TMS"), 2-trimethylsilyl-ethanesulfonyl ("SES"), trityl and substituted trityl groups, allyloxycarbonyl, 9-fluorenylmethyloxycarbonyl ("FMOC"), nitro-veratryloxycarbonyl ("NVOC") and the like. Representative hydroxyl protecting groups include, but are not limited to, those where the hydroxyl group is either acylated (e.g., methyl and ethyl esters, acetate or propionate groups or glycol esters) or alkylated such as benzyl and trityl ethers, as well as alkyl ethers, tetrahydropyranyl ethers, trialkylsilyl ethers (e.g., TMS or TIPPS groups) and allyl ethers.

"Prodrug" refers to a derivative of an active compound (drug) that undergoes a transformation under the conditions of use, such as within the body, to release an active drug. Prodrugs are frequently, but not necessarily, pharmacologically inactive until converted into the active drug. Prodrugs are typically obtained by masking a functional group in the drug believed to be in part required for activity with a progroup (defined below) to form a promoiety or "progroup" which undergoes a transformation, such as cleavage, under the specified conditions of use to release the functional group, and hence the active drug. The cleavage of the promoiety may proceed spontaneously, such as by way of a hydrolysis reaction, or it may be catalyzed or induced by another agent, such as by an enzyme, by light, by acid, or by a change of or exposure to a physical or environmental parameter, such as a change of temperature, or combination thereof. The agent may be endogenous to the conditions of use, such as an enzyme present in the cells to which the prodrug is administered or the acidic conditions of the stomach, or it may be supplied exogenously.

A wide variety of progroups suitable for masking functional groups in active compounds to yield prodrugs are well-known in the art. For example, a hydroxyl functional group may be masked as a sulfonate, ester or carbonate promoiety, which may be hydrolyzed in vitro to provide the hydroxyl group. An amino functional group may be masked as an amide, imine, phosphinyl, phosphonyl, phosphoryl or sulfenyl promoiety, which may be hydrolyzed in vivo to provide the amino group. A carboxyl group may be masked as an ester (including silyl esters and thioesters), amide or hydrazide promoiety, which may be hydrolyzed in vivo to provide the carboxyl group. Other specific examples of suitable progroups and their respective promoieties will be apparent to those of skill in the art.

"Progroup" refers to a type of protecting group that, when used to mask a functional group within an active drug, converts the drug into a prodrug. Progroups are typically attached to the functional group of the drug via bonds that are cleavable under specified conditions of use.

"Substituted," when used to modify a specified group or radical, means that one or more hydrogen atoms of the specified group or radical are each, independently of one another, replaced with the same or different substituent(s). Substituent groups useful for substituting saturated carbon atoms in the specified group or radical include, but are not limited to —$R^a$, halo, —$O^-$, =O, —$OR^b$, —$SR^b$, —$S^-$, =S, —$NR^cR^c$, =$NR^b$, =N—$OR^b$, trihalomethyl, —$CF_3$, —CN, —OCN, —SCN, —NO, —$NO_2$, =$N_2$, —$N_3$, —$S(O)_2R^b$, —$S(O)_2O^-$, —$(CH_2)_{0-4}S(O)_2OR^b$, —$OS(O)_2R^b$, —$OS(O)_2O^-$, —$OS(O)_2OR^b$, —$P(O)(O^-)_2$, —$P(O)(OR^b)(O^-)$, —$P(O)(OR^b)(OR^b)$, —$C(O)R^b$, —$C(S)R^b$, —$C(NR^b)R^b$, —$C(O)O^-$, —$C(O)OR^b$, —$C(S)OR^b$, —$C(O)NR^cR^c$, —$C(NR^b)NR^cR^c$, —$OC(O)R^b$, —$OC(S)R^b$, —$OC(O)O^-$, —$OC(O)OR^b$, —$OC(S)OR^b$, —$NR^bC(O)R^b$, —$NR^bC(S)R^b$, —$NR^bC(O)O^-$, —$NR^bC(O)OR^b$, —$NR^bC(S)OR^b$, —$NR^bC(O)NR^cR^c$, —$NR^bC(NR^b)R^b$ and —$NR^bC(NR^b)NR^cR^c$, where $R^a$ is selected from the group consisting of alkyl, cycloalkyl, heteroalkyl, cycloheteroalkyl, aryl, arylalkyl, heteroaryl and heteroarylalkyl; each $R^b$ is independently hydrogen or $R^a$; and each $R^c$ is independently $R^b$ or alternatively, the two $R^c$s are taken together with the nitrogen atom to which they are bonded form a 5-, 6- or 7-membered cycloheteroalkyl which may optionally include from 1 to 4 of the same or different additional heteroatoms selected from the group consisting of O, N and S. As specific examples, —$NR^cR^c$ is meant to include —$NH_2$, —NH-alkyl, N-pyrrolidinyl and N-morpholinyl.

Similarly, substituent groups useful for substituting unsaturated carbon atoms in the specified group or radical include, but are not limited to, —$R^a$, halo, —$O^-$, —$OR^b$, —$SR^b$, —$S^-$, —$NR^cR^c$, trihalomethyl, —$CF_3$, —CN, —OCN, —SCN, —NO, —$NO_2$, —$N_3$, —$S(O)_2R^b$, —$S(O)_2O^-$, —$S(O)_2OR^b$, —$OS(O)_2R^b$, —$OS(O)_2O^-$, —$OS(O)_2OR^b$, —$P(O)(O^-)_2$, —$P(O)(OR^b)(O^-)$, —$P(O)(OR^b)(OR^b)$, —$C(O)R^b$, —$C(S)R^b$, —$C(NR^b)R^b$, —$C(O)O^-$, —$C(O)OR^b$, —$C(S)OR^b$, —$C(O)NR^cR^c$, —$C(NR^b)NR^cR^c$, —$OC(O)R^b$, —$OC(S)R^b$, —$OC(O)O^-$, —$OC(O)OR^b$, —$OC(S)OR^b$, —$NR^bC(O)R^b$, —$NR^bC(S)R^b$, —$NR^bC(O)O^-$, —$NR^bC(O)OR^b$, —$NR^bC(S)OR^b$, —$NR^bC(O)NR^cR^c$, —$NR^bC(NR^b)R^b$ and —$NR^bC(NR^b)NR^cR^c$, where $R^a$, $R^b$ and $R^c$ are as previously defined.

Substituent groups useful for substituting nitrogen atoms in heteroalkyl and cycloheteroalkyl groups include, but are not limited to, —$R^a$, —$O^-$, —$OR^b$, —$SR^b$, —$S^-$, —$NR^cR^c$, trihalomethyl, —$CF_3$, —CN, —NO, —$NO_2$, —$S(O)_2R^b$, —$S(O)_2O^-$, —$S(O)_2OR^b$, $OS(O)_2R^b$, —$OS(O)_2O^-$, —$OS(O)_2OR^b$, —$P(O)(O^-)_2$, —$P(O)(OR^b)(O^-)$, —$P(O)(OR^b)(OR^b)$, —$C(O)R^b$, —$C(S)R^b$, —$C(NR^b)R^b$—$C(O)OR^b$, —$C(S)OR^b$, —$C(O)NR^cR^c$, —$C(NR^b)NR^cR^c$, —$OC(O)R^b$, —$OC(S)R^b$, —$OC(O)OR^b$, —$OC(S)OR^b$, —$NR^bC(O)R^b$, —$NR^bC(S)R^b$, —$NR^bC(O)OR^b$, —$NR^bC(S)OR^b$, —$NR^bC(O)NR^cR^c$, —$NR^bC(NR^b)R^b$ and —$NR^bC(NR^b)NR^cR^c$, where $R^a$, $R^b$ and $R^c$ are as previously defined.

Substituent groups from the above lists useful for substituting other specified groups or atoms will be apparent to those of skill in the art.

The substituents used to substitute a specified group can be further substituted, typically with one or more of the same or different groups selected from the various groups specified above.

"Syk Kinase" refers to the well-known 72 kDa non-receptor (cytoplasmic) spleen protein tyrosine kinase expressed in B-cells and other hematopoetic cells. Syk kinase includes two consensus Src-homology 2 (SH2) domains in tandem that bind to phosphorylated immunoreceptor tyrosine-based activation motifs ("ITAMs"), a "linker" domain and a catalytic domain (for a review of the structure and function of Syk kinase see Sada et al., 2001, J. Biochem. (Tokyo) 130:177-186); see also Turner et al., 2000, Immunology Today 21:148-154). Syk kinase has been extensively studied as an effector of B-cell receptor (BCR) signaling (Turner et al., 2000, supra). Syk kinase is also critical for tyrosine phosphorylation of multiple proteins which regulate important pathways leading from immunoreceptors, such as $Ca^{2+}$ mobilization and mitogen-activated protein kinase (MAPK) cascades and degranulation. Syk kinase also plays a critical role in integrin signaling in neutrophils (see, e.g., Mocsai et al. 2002, Immunity 16:547-558).

As used herein, Syk kinase includes kinases from any species of animal, including but not limited to, homosapiens, simian, bovine, porcine, rodent, etc., recognized as belonging to the Syk family. Specifically included are isoforms, splice variants, allelic variants, mutants, both naturally occurring and man-made. The amino acid sequences of such Syk kinases are well known and available from GENBANK. Specific examples of mRNAs encoding different isoforms of human Syk kinase can be found at GENBANK accession no. gi|213615521|ref|NM_003177.2|, gi|496899|emb|Z29630.1||HSSYKPTK[496899] and gi|15030258|gb|BC011399.1 |BC011399[15030258].

As used herein, the term "subject" encompasses mammals and non-mammals. Examples of mammals include, but are not limited to, any member of the Mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. Examples of non-mammals include, but are not limited to, birds, fish and the like. The term does not denote a particular age or gender.

As used herein, the terms "treat" or "treatment" are used interchangeably and are meant to indicate a postponement of development of a disease and/or a reduction in the severity of such symptoms that will or are expected to develop, where the disease is associated with the functioning of a kinase. The terms further include ameliorating existing symptoms, preventing additional symptoms, and ameliorating or preventing the underlying metabolic causes of symptoms.

The compounds of the present invention may be used to inhibit or reduce the activity of kinases. In these contexts, inhibition and reduction of activity of kinases refers to a lower level of the measured activity relative to a control experiment in which the cells or the subjects are not treated with the test compound. In particular aspects, the inhibition or reduction in the measured activity is at least a 10% reduction or inhibition. One of skill in the art will appreciate that reduction or inhibition of the measured activity of at least 20%, 50%, 75%, 90% or 100%, or any number in between, may be preferred for particular applications.

The Compounds

As described in the Summary, the instant disclosure provides prodrugs of biologically active 2,4-pyrimidinediamine compounds, such as the various 2,4-pyrimidinediamine compounds described in U.S. application Ser. No. 10/355,543 filed Jan. 31, 2003 (US2004/0029902A1), international application Serial No. PCT/US03/03022 filed Jan. 31, 2003 (WO 03/063794), U.S. application Ser. No. 10/631,029 filed Jul. 29, 2003, international application Serial No. PCT/US03/24087 (WO2004/014382), U.S. application Ser. No. 10/903,263 filed Jul. 30, 2004 (US2005/0234049), and international application Serial No. PCT/US2004/24716 (WO2005/016893). Prodrugs of the pyrimidine-2,4-diamine compounds are of particular interest, as these compounds inhibit kinases, such as inhibiting upstream Fc receptor signaling cascades as well as Syk kinase and Syk kinase-dependent signaling cascades. The prodrugs generally include such active 2,4-pyrimidinediamine compounds in which one or more of the available primary or secondary amine groups is masked with a progroup $R^P$ that metabolizes in vivo by way of the corresponding hydroxy, thio- or amino-methylamine intermediated to yield the active 2,4-pyrimidinediamine drug.

The invention provides novel compounds containing the pyrimidine-2,4-diamine moiety, and compositions comprising the compounds. In one aspect, the compounds of the invention have the formula (I)

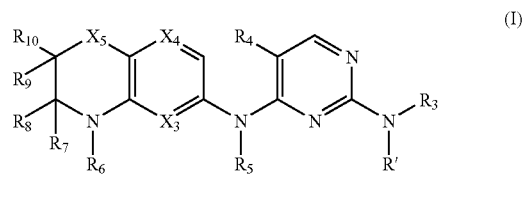

(I)

wherein $R_3$ is aryl or heteroaryl that is optionally substituted; $X_3$ and $X_4$ are independently selected from CH or N; $X_5$ is selected from the group consisting of $CR_{12}R_{13}$, O, S, SO, $SO_2$, and $NR_{14}$, wherein $R_{12}$ and $R_{13}$ are independently selected from H, OH, or lower alkyl; $R_4$ is an electronegative group; R', $R_5$, $R_6$ and $R_{14}$ are independently selected from H, lower alkyl, a progroup, cycloalkyl or aryl, and wherein at least one of R', $R_5$, $R_6$ or $R_{14}$ is the aforementioned progroup linked via a constitutent carbamate, a thiocarbamate, a dithiocarbamate, a urea, or a thiourea linkage; $R_7$ and $R_8$ are independently selected from the group consisting of H, halogen, lower alkyl, cycloalkyl, aryl, and heteroaryl; and $R_9$ and $R_{10}$ are independently selected from the group consisting of H, halogen, —OH, -alkoxy, lower alkyl, cycloalkyl, aryl, and heteroaryl; wherein $R_7$ and $R_8$, or $R_9$ and $R_{10}$ together form an oxo group, and provided $R_9$ or $R_{10}$ are not —OH or alkoxy when $X_5$ is $NR_{14}$.

The nature of the progroup can vary, and will depend upon, among other factors, the desired water solubility of the prodrug, its intended mode of administration and/or its intended mechanism or site of metabolism to the active 2,4-pyrimidinediamine compound. The identity of the $R^3$ group can also be selected so as to impart the prodrug with desirable characteristics. For example, lipophilic groups can be used to decrease water solubility and hydrophilic groups can be used to increase water solubility. In this way, prodrugs specifically tailored for selected modes of administration can be obtained. The $R^3$ group can also be designed to impart the prodrug with other properties, such as, for example, improved passive intestinal absorption, improved transport-mediated intestinal absorption, protection against fast metabolism (slow-release prodrugs), tissue-selective delivery, passive enrichment in target tissues, targeting-specific transporters, etc. Groups capable of imparting prodrugs with these characteristics are well-known, and are described, for example, in Ettmayer et al. (2004) J. Med. Chem. 47: 2393-2404. All of the various groups described in these references can be utilized in the prodrugs described herein.

The suitability of any particular progroup for a desired mode of administration can be confirmed in biochemical assays. For example, if a prodrug is to be administered by injection into a particular tissue or organ, and the identities of the various enzyme(s) expressed in the tissue or organ are known, the particular prodrug can be tested for metabolism in biochemical assays with the isolated enzyme(s). Alternatively, the particular prodrug can be tested for metabolism to the active 2,4-pyrimidinediamine compound with tissue and/or organ extracts. Using tissue and/or organ extracts can be of particular convenience when the identity(ies) of the enzymes expressed in the target tissues or organs are unknown, or in instances when the isolated enzymes are not conveniently available. Skilled artisans will be able to readily select progroups having metabolic properties (such as kinetics) suitable for particular applications using such in vitro tests. The specific prodrugs could also be tested for suitable metabolism in in vitro animal models.

In another aspect, the present invention provides compounds of formula (II)

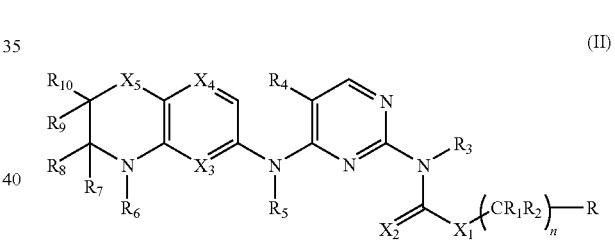

(II)

wherein $X_1$ is O, S, or $NR_{11}$; $X_2$ is selected from the group consisting of O and S; $X_3$ and $X_4$ are independently selected from CH or N; $X_5$ is selected from the group consisting of $CR_{12}R_{13}$, O, S, SO, $SO_2$, and $NR_{14}$ wherein $R_{12}$ and $R_{13}$ are independently selected from H, OH, lower alkyl, or together form an oxo; and $R_{14}$ is H or lower alkyl; R is selected from the group consisting of straight or branched, saturated or unsaturated alkyl, allyl, cycloalkyl, cycloalkyl, cycloheteroalkyl, aryl, heteroaryl, prenylalkaryl and heteroarylalkyl, each of which is optionally substituted; $R_1$ and $R_2$ are each independently selected from the group consisting of H, OH, —$OR_{11}$, $NR_{15}R_{15}$, halo, lower alkyl, —C(O)O-alkyl, —C(O)OH, —OP(=O)(OR_{11})_2, —OC(=O)OR_{11}, —OC(=O)R_{11}, cycloalkyl, aryl, heteroaryl or together form an oxo, wherein each $R_{15}$ is independently selected from H, lower alkyl, prenyl, allyl, —C(O)O-alkyl, cycloalkyl, aryl, heteroaryl, alkaryl and alkheteroaryl, or two of $R_{15}$ combine to form an optionally substituted cycloheteroalkyl; $R_3$ is aryl or heteroaryl, each optionally substituted; each $R_{11}$ is independently H or lower alkyl; $R_4$ is an electronegative group such as $NO_2$, fluorine, halogen, CN, haloalkyl, alkoxy, carboxylate, $CF_3$, $CHF_2$, $CH_2F$, $CF_3O$—, and the like; $R_5$ and $R_6$ are independently selected from H, lower alkyl, cycloalkyl or aryl; $R_7$, $R_8$, $R_9$, and $R_{10}$ are independently selected from the group consisting of H, OH, halogen, lower alkyl, cycloalkyl, aryl, and heteroaryl, or wherein $R_7$ and $R_8$ or $R_9$ and $R_{10}$ together form an oxo group; and n is an integer from 0 to 10.

In another aspect, the present invention provides compounds of formula (III):

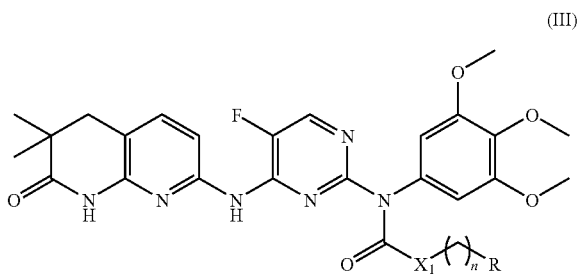

(III)

wherein $X_1$ is O or $NR_{11}$; R is selected from the group consisting of straight or branched, saturated or unsaturated alkyl, allyl, cycloalkyl, cycloheteroalkyl, aryl, and heteroaryl; and n is and integer between 0 and 10. Thus, for example, R can be morpholine, 1-methylpiperidine, piperazine, 4-(3-propane-1-sulfonic acid) piperazin-1-yl, dimethylamino, tryptamine, N-tert-butylaceyltryptamine, phosphate, methyl phosphate, dimethyl phosphate, phosphonate, and the like. Exemplary prodrugs are described in Examples 1-10 and in FIG. 1.

In examples 1-10, (also as depicted in Schemes 1-3) a carbamoyl chloride is produced which is then used to make prodrugs of the invention. Also, as depicted in FIG. 1, haloalkyl carbamate intermediates, for example but not limited to intermediate 10 where the carbamate is on the N2-nitrogen, can be made at various positions on the 2,4-pyrimidinediamine and further converted into prodrugs of the invention. For example, chloromethyl ether carbamates can be reacted with imines, like pyridine, to make pyridinium salt prodrugs, 11. In another example, chloromethyl ether carbamates can be reacted with alcohols or alkoxides to make acetal-carbamate prodrugs, 12. In another example, chloromethyl ether carbamates can be reacted with silver phosphonate salts to make mixed phosphate-acetal-carbamate prodrugs, 13. In another example, chloromethyl ether carbamates can be reacted with carboxylate salts to make ester-acetal-carbamate prodrugs, 14.

Those of skill in the art will appreciate that the compounds of the invention described herein may include functional groups that can be masked with progroups to create prodrugs. Such prodrugs are usually, but need not be, pharmacologically inactive until converted into their active drug form. In the prodrugs of the invention, any available functional moiety may be masked with a progroup to yield a prodrug. Myriad progroups suitable for masking such functional groups to yield promoieties that are cleavable under the desired conditions of use are known in the art.

Methods of Synthesis

The compounds of the invention comprise isoxazoloanthrones, as described above. The compounds can be obtained from commercial sources, such as Aldrich Chemical Co. (Milwaukee, Wis.), Sigma Chemical Co. (St. Louis, Mo.), or Maybridge (Cornwall, England), or the compounds can be synthesized. The compounds of the present invention, and other related compounds having different substituents identified by any of the methods described above can be synthesized using techniques and materials known to those of skill in the art, such as described, for example, in March, ADVANCED ORGANIC CHEMISTRY 4$^{th}$ Ed., (Wiley 1992); Carey and Sundberg, ADVANCED ORGANIC CHEMISTRY 3$^{rd}$ Ed., Vols. A and B (Plenum 1992), and Green and Wuts, PROTECTIVE GROUPS IN ORGANIC SYNTHESIS 2$^{nd}$ Ed. (Wiley 1991). Starting materials useful for preparing compounds of the invention and intermediates thereof are commercially available or can be prepared by well-known synthetic methods (see, e.g., Harrison et al., "Compendium of Synthetic Organic Methods", Vols. 1-8 (John Wiley and Sons, 1971-1996); "Beilstein Handbook of Organic Chemistry," Beilstein Institute of Organic Chemistry, Frankfurt, Germany; Feiser et al., "Reagents for Organic Synthesis," Volumes 1-21, Wiley Interscience; Trost et al., "Comprehensive Organic Synthesis," Pergamon Press, 1991; "Theilheimer's Synthetic Methods of Organic Chemistry," Volumes 1-45, Karger, 1991; March, "Advanced Organic Chemistry," Wiley Interscience, 1991; Larock "Comprehensive Organic Transformations," VCH Publishers, 1989; Paquette, "Encyclopedia of Reagents for Organic Synthesis," 3d Edition, John Wiley & Sons, 1995). Other methods for synthesis of the compounds described herein and/or starting materials are either described in the art or will be readily apparent to the skilled artisan. Alternatives to the reagents and/or protecting groups may be found in the references provided above and in other compendiums well known to the skilled artisan. Guidance for selecting suitable protecting groups can be found, for example, in Greene & Wuts, "Protective Groups in Organic Synthesis," Wiley Interscience, 1999. Accordingly, the synthetic methods and strategy presented herein are illustrative rather than comprehensive.

The compounds and intermediates described herein can be synthesized via a variety of different synthetic routes using commercially available starting materials and/or starting materials prepared by conventional synthetic methods. Suitable exemplary methods that may be routinely used and/or adapted to synthesize active 2,4-pyrimidinediamine compounds can be found in U.S. Pat. No. 5,958,935, U.S. application Ser. No. 10/355,543 filed Jan. 31, 2003 (US2004/0029902A1), international application Serial No. PCT/US03/03022 filed Jan. 31, 2003 (WO 03/063794), U.S. application Ser. No. 10/631,029 filed Jul. 29, 2003, international application Serial No. PCT/US03/24087 (WO2004/014382), U.S. application Ser. No. 10/903,263 filed Jul. 30, 2004 (US2005/0234049), and international application Serial No. PCT/US2004/24716 (WO2005/016893). These active 2,4-pyrimidinediamine compounds can be used as starting materials to synthesize the prodrugs.

Thus, for example, the compounds of the invention having carbamate, thiocarbamate, or urea linkages can be synthesized using the reactions shown in Scheme 1 below:

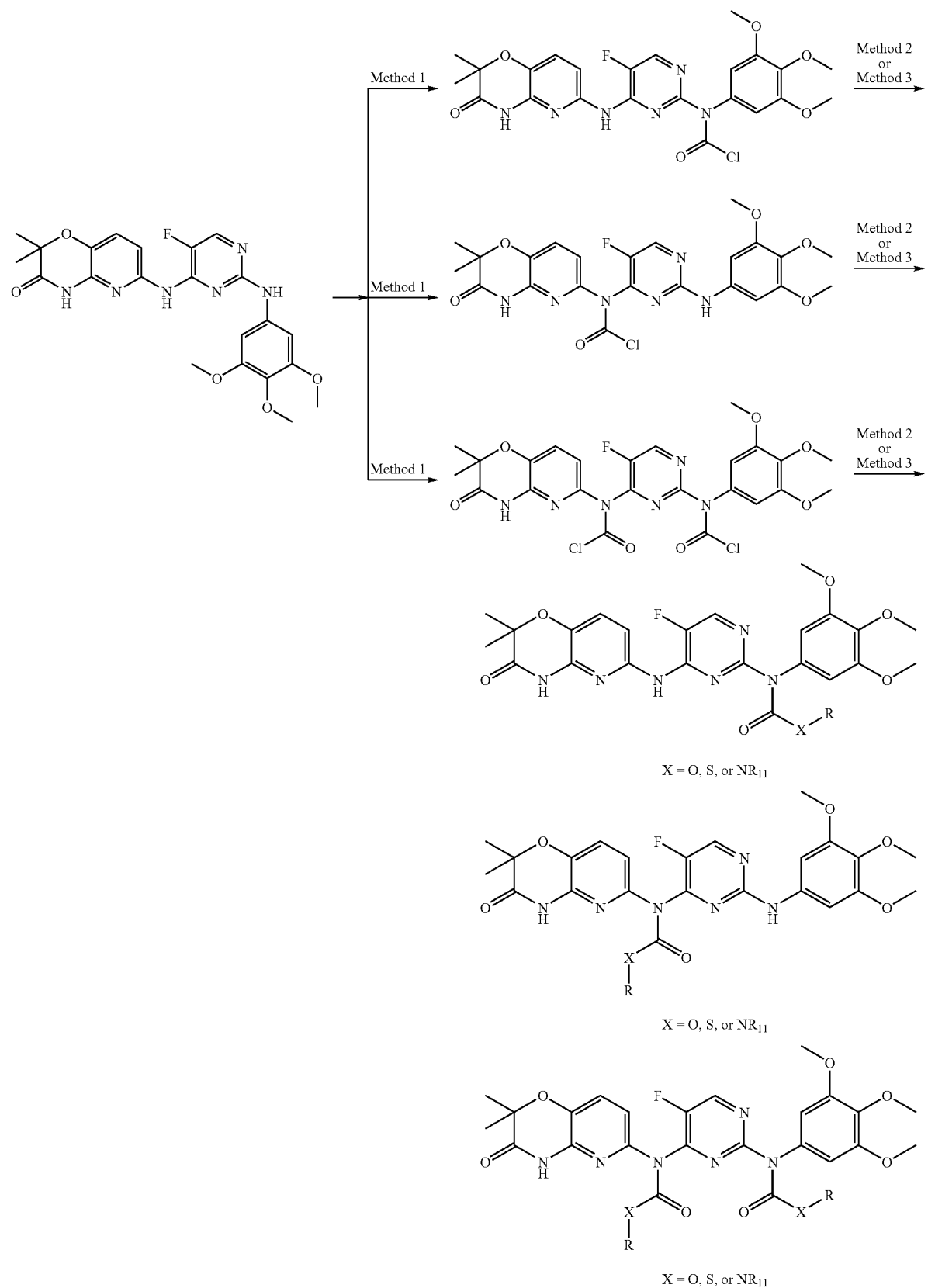

-continued

Method 1:
Bases: NEt₃, pyridine, 2-6-lutidine, i-Pr₂NEt, NaHCO₃, KHCO₃
Reagents: phosgene, triposgene
Solvents: CH₂Cl₂, toluene; ClCH₂CH₂Cl, THF Method 2:
Bases: NEt₃, pyridine, i-Pr₂NEt;
Reagents: RXH
Solvents: CH₂Cl₂, ClCH₂CH₂Cl, THF, DMF, CH₃CN;
Catalyst: 4-DMAP Method 3:
Bases: n-BuLi, NaH, KH, t-BuOK, (Me₃Si)₂NLi, (Me₃Si)₂NNa, (Me₃Si)₂NK, NaHCO₃, KHCO₃, K₂CO₃;
Reagents: RXH
Solvents: THF, DMF The compounds of the invention having thiocarbamate, dithiocarbamate, or thiourea linkages can be synthesized using the reactions shown in Scheme 2 below:

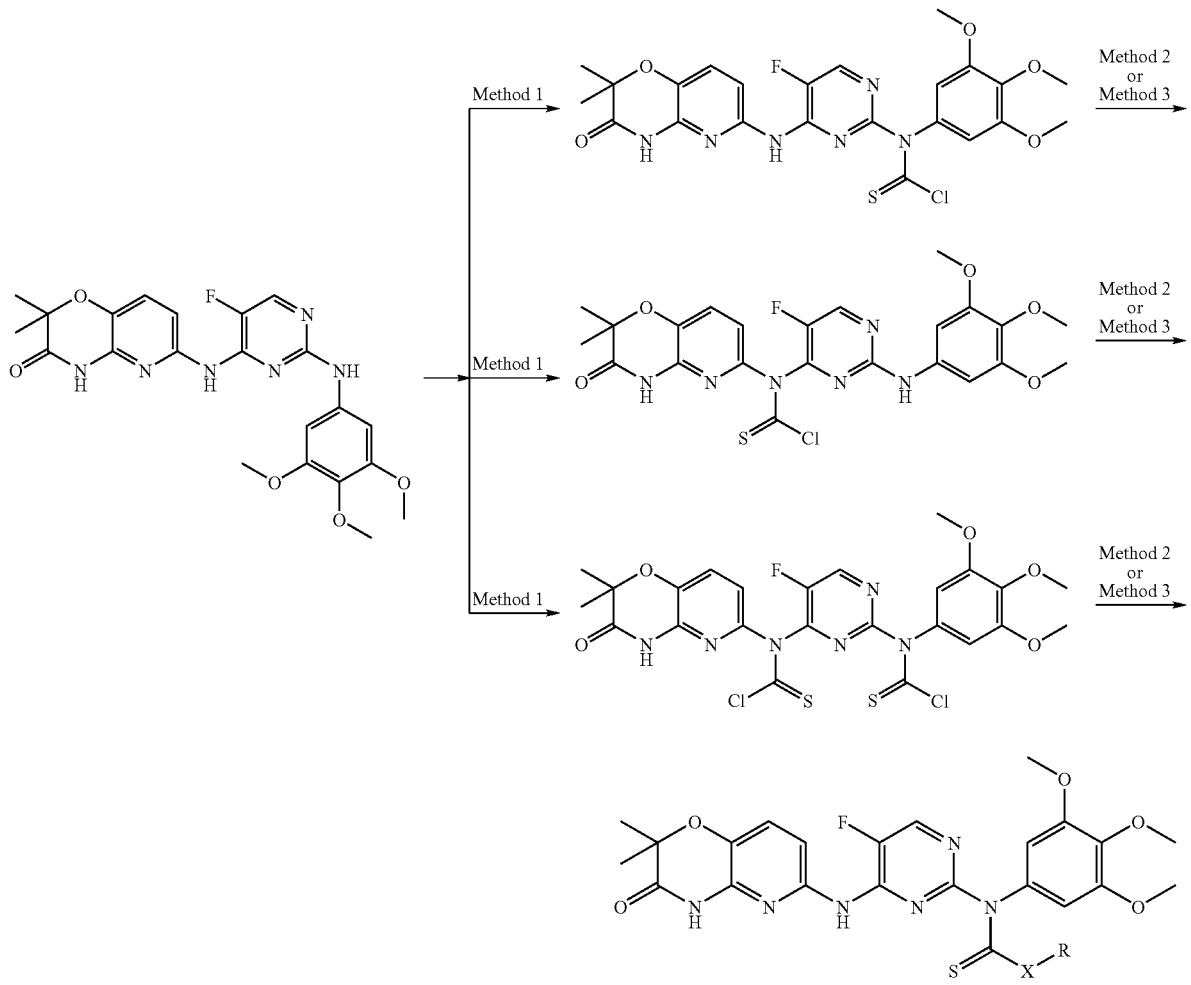

Scheme 2.

-continued

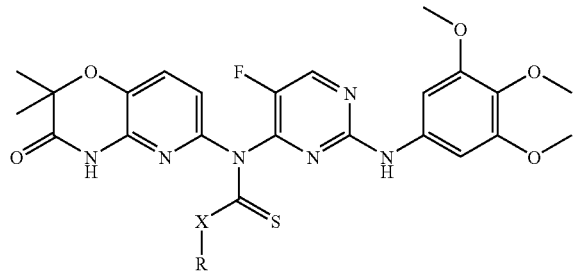

X = O, NH or S

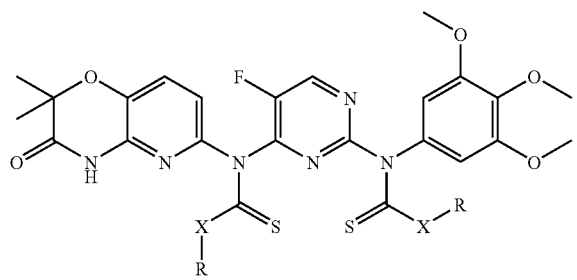

X = O, NH or S

Method 1:
    Bases:      NEt$_3$, pyridine, 2-6-lutidine, i-Pr$_2$NEt, NaHCO$_3$, KHCO$_3$
    Reagents:  thiophosgene
    Solvents:   CH$_2$Cl$_2$, toluene; ClCH$_2$CH$_2$Cl, THF Method 2:
    Bases:      NEt$_3$, pyridine, i-Pr$_2$NEt;
    Reagents:  RXH
    Solvents:   CH$_2$Cl$_2$, ClCH$_2$CH$_2$Cl, THF, DMF, CH$_3$CN,
    Catalyst:  4-DMAP Method 3:
    Bases:      n-BuLi, NaH, KH, t-BuOK, (Me$_3$Si)$_2$NLi, (Me$_3$Si)$_2$NNa,
               (Me$_3$Si)$_2$NK, NaHCO$_3$, KHCO$_3$, K$_2$CO$_3$;
    Reagents:  RXH
    Solvents:   THF, DMF Alternative methods for the synthesis of compounds of the invention having thiocarbamate, dithiocarbamate, or thiourea linkages is shown in Scheme 3 below:

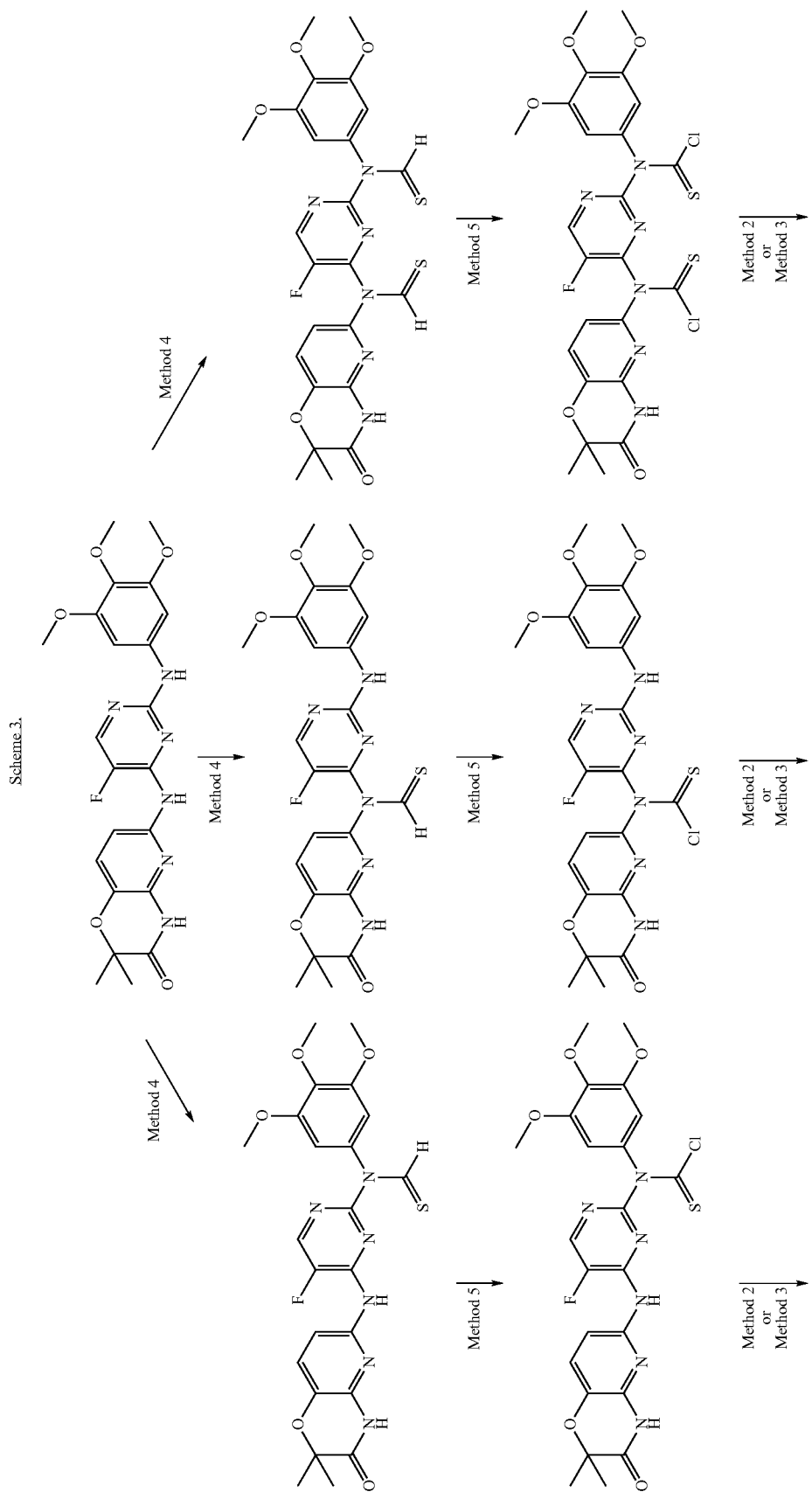

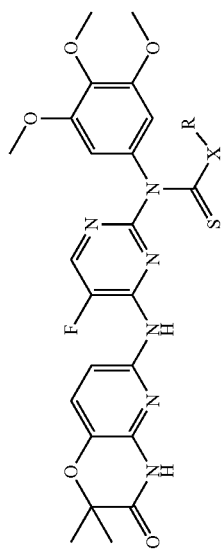

-continued

X = O, S, or NR₁₁

X = O, S, or NR₁₁

X = O, S, or NR₁₁

Method 5:
SCl₂/pyridine or SO₂Cl₂

Method 3:
Bases: n-BuLi, NaH, KH, t-BuOK, (Me₃Si)₂NLi, (Me₃Si)₂NNa, (Me₃Si)₂NK, NaHCO₃, KHCO₃, K₂CO₃;
Reagents: RXH
Solvents: THF, DMF;

Method 4:
HC(S)NMe₂
solvent: benzene, toluene, dioxane, THF, acetone, CH₃CN
or
HO₂CC(O)CO₂H/S
solvent: benzene, toluene, dioxane, THF, acetone, CH₃CN Method 2:
Bases: NEt₃, pyridine, i-Pr₂NEt;
Reagents: RXH
Solvents: CH₂Cl₂, ClCH₂CH₂Cl, THF, DMF, CH₃CN;
Catalyst: 4-DMAP The procedures described herein for synthesizing the compounds of the invention may include one or more steps of protection and deprotection (e.g., the formation and removal of acetal groups). In addition, the synthetic procedures disclosed below can include various purifications, such as column chromatography, flash chromatography, thin-layer chromatography (TLC), recrystallization, distillation, high-pressure liquid chromatography (HPLC) and the like. Also, various techniques well known in the chemical arts for the identification and quantification of chemical reaction products, such as proton and carbon-13 nuclear magnetic resonance ($^1$H and $^{13}$C NMR), infrared and ultraviolet spectroscopy (IR and UV), X-ray crystallography, elemental analysis (EA), HPLC and mass spectroscopy (MS) can be used as well. Methods of protection and deprotection, purification and identification and quantification are well known in the chemical arts.

Indications

Compounds of the present invention are useful for, but not limited to, the prevention or treatment of cancer and related diseases. The compounds of the invention have kinase inhibitory activity, such as Syk kinase inhibitory activity, Src kinase inhibitory activity, IGF-1R inhibitory activity, and the like. The compounds of the invention are useful in therapy as antineoplasia agents.

In vitro and cellular assays suitable for confirming the activity of a particular 2,4-pyrimidinediamine compound are described in detail in U.S. application Ser. No. 10/355,543 filed Jan. 31, 2003 (US2004/0029902A1), international application Serial No. PCT/US03/03022 filed Jan. 31, 2003 (WO 03/063794), U.S. application Ser. No. 10/631,029 filed Jul. 29, 2003, international application Serial No. PCT/US03/24087 (WO2004/014382), U.S. application Ser. No. 10/903,263 filed Jul. 30, 2004 (US2005/0234049), and international application Serial No. PCT/US2004/24716 (WO2005/016893).

The ability of a particular prodrug to metabolize to an active 2,4-pyrimidinediamine compound under the desired conditions of use can be confirmed in in vitro and/or in vivo assays, as previously described.

Compounds of the invention can be useful for the treatment of neoplasia including cancer and metastasis, including, but not limited to: carcinoma such as cancer of the bladder, breast, colon, kidney, liver, lung (including small cell lung cancer), esophagus, gall-bladder, ovary, pancreas, stomach, cervix, thyroid, prostate, and skin (including squamous cell carcinoma); hematopoietic tumors of lymphoid lineage (including leukemia, acute lymphocitic leukemia, acute lymphoblastic leukemia, B-cell lymphoma, T-cell-lymphoma, Hodgkin's lymphoma, non-Hodgkin's lymphoma, hairy cell lymphoma and Burkett's lymphoma); hematopoietic tumors of myeloid lineage (including acute and chronic myelogenous leukemias, myelodysplastic syndrome and promyelocytic leukemia); tumors of mesenchymal origin (including fibrosarcoma and rhabdomyosarcoma, and other sarcomas, e.g. soft tissue and bone); tumors of the central and peripheral nervous system (including astrocytoma, neuroblastoma, glioma and schwannomas); and other tumors (including melanoma, seminoma, teratocarcinoma, osteosarcoma, xenoderoma pigmentosum, keratoctanthoma, thyroid follicular cancer and Kaposi's sarcoma). The compounds of the present invention are also useful in the treatment of cancer related indications such as solid tumors, sarcomas (especially Ewing's sarcoma and osteosarcoma), retinoblastoma, rhabdomyosarcomas, neuroblastoma, hematopoietic malignancies, including leukemia and lymphoma, tumor-induced pleural or pericardial effusions, and malignant ascites.

The compounds of the present invention can also be useful for promoting apoptosis.

The compounds of this invention can also act as inhibitors of other protein kinases, e.g. ErbB, KDR, CDK-2, LCK, CDK-5, IKK, JNK3, and thus be effective in the treatment of diseases associated with other protein kinases.

Besides being useful for human treatment, these compounds are also useful for veterinary treatment of companion animals, exotic animals and farm animals, including mammals, rodents, and the like. More preferred animals include horses, dogs, and cats. As used herein, the compounds of the present invention include the pharmaceutically acceptable derivatives thereof.

Uses and Administration

The compounds of the invention and/or compositions thereof find particular use in the treatment and/or prevention diseases in animals and humans caused by kinases. When used in this context, the compounds may be administered per se, but are typically formulated and administered in the form of a pharmaceutical composition. The exact composition will depend upon, among other things, the method of administration and will apparent to those of skill in the art. A wide variety of suitable pharmaceutical compositions are described, for example, in *Remington's Pharmaceutical Sciences*, 20$^{th}$ ed., 2001).

Pharmaceutical compositions may take a form suitable for virtually any mode of administration, including, for example, topical, ocular, oral, buccal, systemic, nasal, injection, transdermal, rectal, vaginal, etc., or a form suitable for administration by inhalation or insufflation.

Formulations suitable for oral administration can consist of (a) liquid solutions, such as an effective amount of the active compound suspended in diluents, such as water, saline or PEG 400; (b) capsules, sachets or tablets, each containing a predetermined amount of the active ingredient, as liquids, solids, granules or gelatin; (c) suspensions in an appropriate liquid; and (d) suitable emulsions. Tablet forms can include one or more of lactose, sucrose, mannitol, sorbitol, calcium phosphates, corn starch, potato starch, microcrystalline cellulose, gelatin, colloidal silicon dioxide, talc, magnesium stearate, stearic acid, and other excipients, colorants, fillers, binders, diluents, buffering agents, moistening agents, preservatives, flavoring agents, dyes, disintegrating agents, and pharmaceutically compatible carriers. Lozenge forms can comprise the active ingredient in a flavor, e.g., sucrose, as well as pastilles comprising the active ingredient in an inert base, such as gelatin and glycerin or sucrose and acacia emulsions, gels, and the like containing, in addition to the active ingredient, carriers known in the art.

The compound of choice, alone or in combination with other suitable components, can be made into aerosol formulations (i.e., they can be "nebulized") to be administered via inhalation. Aerosol formulations can be placed into pressurized acceptable propellants, such as dichlorodifluoromethane, propane, nitrogen, and the like.

Suitable formulations for rectal administration include, for example, suppositories, which consist of the packaged nucleic acid with a suppository base. Suitable suppository bases include natural or synthetic triglycerides or paraffin hydrocarbons. In addition, it is also possible to use gelatin rectal capsules which consist of a combination of the compound of choice with a base, including, for example, liquid triglycerides, polyethylene glycols, and paraffin hydrocarbons.

Formulations suitable for parenteral administration, such as, for example, by intraarticular (in the joints), intravenous, intramuscular, intradermal, intraperitoneal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. In the practice of this invention, compositions can be administered, for example, by intravenous infusion, orally, topically, intraperitoneally, intravesically or intrathecally. Parenteral administration, oral administration, subcutaneous administration and intravenous administration are the preferred methods of administration. A specific example of a suitable solution formulation may comprise from about 0.5-100 mg/ml compound and about 1000 mg/ml propylene glycol in water. Another specific example of a suitable solution formulation may comprise from about 0.5-100 mg/ml compound and from about 800-1000 mg/ml polyethylene glycol 400 (PEG 400) in water.

A specific example of a suitable suspension formulation may include from about 0.5-30 mg/ml compound and one or more excipients selected from the group consisting of: about 200 mg/ml ethanol, about 1000 mg/ml vegetable oil (e.g., corn oil), about 600-1000 mg/ml fruit juice (e.g., grapefruit juice), about 400-800 mg/ml milk, about 0.1 mg/ml carboxymethylcellulose (or microcrystalline cellulose), about 0.5 mg/ml benzyl alcohol (or a combination of benzyl alcohol and benzalkonium chloride) and about 40-50 mM buffer, pH 7 (e.g., phosphate buffer, acetate buffer or citrate buffer or, alternatively 5% dextrose may be used in place of the buffer) in water.

A specific example of a suitable liposome suspension formulation may comprise from about 0.5-30 mg/ml compound, about 100-200 mg/ml lecithin (or other phospholipid or mixture of phospholipids) and optionally about 5 mg/ml cholesterol in water.

The formulations of compounds can be presented in unit-dose or multi-dose sealed containers, such as ampules and vials. Injection solutions and suspensions can be prepared from sterile powders, granules, and tablets of the kind previously described.

The pharmaceutical preparation is preferably in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form. The composition can, if desired, also contain other compatible therapeutic agents, discussed in more detail, below.

In therapeutic use, the compounds utilized in the pharmaceutical method of the invention are administered to patients at dosage levels suitable to achieve therapeutic benefit. By therapeutic benefit is meant that the administration of compound leads to a beneficial effect in the patient over time.

Initial dosages suitable for administration to humans may be determined from in vitro assays or animal models. For example, an initial dosage may be formulated to achieve a serum concentration that includes the $IC_{50}$ of the particular compound being administered, as measured in an in vitro assay. Alternatively, an initial dosage for humans may be based upon dosages found to be effective in animal models of the disease. As one example, the initial dosage may be in the range of about 0.01 mg/kg/day to about 200 mg/kg/day, or about 0.1 mg/kg/day to about 100 mg/kg/day, or about 1 mg/kg/day to about 50 mg/kg/day, or about 10 mg/kg/day to about 50 mg/kg/day, can also be used. The dosages, however, may be varied depending upon the requirements of the patient, the severity of the condition being treated, and the compound being employed. The size of the dose also will be determined by the existence, nature, and extent of any adverse side-effects that accompany the administration of a particular compound in a particular patient. Determination of the proper dosage for a particular situation is within the skill of the practitioner. Generally, treatment is initiated with smaller dosages which are less than the optimum dose of the compound. Thereafter, the dosage is increased by small increments until the optimum effect under circumstances is reached. For convenience, the total daily dosage may be divided and administered in portions during the day, if desired.

Combination Therapy

In certain embodiments of the present invention, the compounds of the invention and/or compositions thereof can be used in combination therapy with at least one other therapeutic agent. A compound of the invention and/or composition thereof and the therapeutic agent can act additively or, more preferably, synergistically.

While the compounds of the invention can be administered as the sole active pharmaceutical agent, they can also be used in combination with one or more compounds of the invention or other agents. When administered as a combination, the therapeutic agents can be formulated as separate compositions that are administered at the same time or sequentially at different times, or the therapeutic agents can be given as a single composition.

Co-administration of a compound of the present invention and another pharmaceutical agent is intended to embrace administration of each agent in a sequential manner in a regimen that will provide beneficial effects of the drug combination, and is intended as well to embrace co-administration of these agents in a substantially simultaneous manner, such as in a single capsule having a fixed ratio of these active agents or in multiple, separate capsules for each agent.

Specifically, the administration of compounds of the present invention may be in conjunction with additional therapies known to those skilled in the art in the prevention or treatment of neoplasia, such as with radiation therapy or with cytostatic or cytotoxic agents.

If formulated as a fixed dose, such combination products employ the compounds of this invention within the accepted dosage ranges. Compounds of Formulae I, II, or III can also be administered sequentially with known anticancer or cytotoxic agents when a combination formulation is inappropriate. The invention is not limited in the sequence of administration; compounds of formula I may be administered either prior to or after administration of the known anticancer or cytotoxic agent.

There are large numbers of antineoplastic agents available in commercial use, in clinical evaluation and in pre-clinical development, which would be selected for treatment of neoplasia by combination drug chemotherapy. Such antineoplastic agents fall into several major categories, namely, antibiotic-type agents, alkylating agents, antimetabolite agents, hormonal agents, immunological agents, interferon-type agents and a category of miscellaneous agents.

In one aspect, the compounds of the invention can be co-administered with antimetabolite-type/thymidilate synthase inhibitor antineoplastic agents. Suitable antimetabolite antineoplastic agents can be selected from but not limited to the group consisting of 5-FU-fibrinogen, acanthifolic acid, aminothiadiazole, brequinar sodium, carmofur, Ciba-Geigy CGP-30694, cyclopentyl cytosine, cytarabine phosphate stearate, dezaguanine, dideoxycytidine, dideoxyguanosine, didox, doxifluridine, fazarabine, floxuridine, isopropyl pyrrolizine, methotrexate, uricytin, and the like In another aspect, the compounds of the invention can be co-administered with alkylating-type antineoplastic agents. Suitable alkylating-type antineoplastic agents can be selected from but not limited to the group consisting of altretamine, anaxirone, bestrabucil, budotitane, carboplatin, carmustine, chlorambucil, cisplatin, cyclophosphamide, diplatinum cytostatic, elmustine, fotemustine, tauromustine, temozolomide, teroxirone, tetraplatin, trimelamol, and the like.

In one aspect, the compounds of the invention can be co-administered with antibiotic-type antineoplastic agents. Suitable antibiotic-type antineoplastic agents can be selected from but not limited to the group consisting of aclarubicin, actinomycin D, actinoplanone, anthracycline, bleomycin sulfate, bryostatin-1, calichemycin, chromoximycin, dactinomycin, daunorubicin, doxorubicin, doxorubicin-fibrinogen, erbstatin, esorubicin, glidobactin, herbimycin, idarubicin, illudins, oxalysine, oxaunomycin, sparsomycin, thrazine, zorubicin, and the like.

In one aspect, the compounds of the invention can be co-administered with other antineoplastic agents, including tubulin interacting agents, topoisomerase II inhibitors, topoisomerase I inhibitors and hormonal agents, selected from but not limited to the group consisting of α-carotene, α-difluoromethyl-arginine, acitretin, amonafide, ankinomycin, antineoplaston A5, asparaginase, Avarol, bromofosfamide, caracemide, claviridenone, cytochalasin B, cytarabine, cytocytin, dacarbazine, paclitaxel, Efamol porphyrin, spirogermanium, taxol, thaliblastine, vinblastine sulfate, and the like.

The invention relates to inhibitors of enzymes that catalyze phosphoryl transfer and/or that bind ATP/GTP nucleotides, compositions comprising the inhibitors, and methods of using the inhibitors and inhibitor compositions. The inhibitors and compositions comprising them are useful for treating or modulating disease in which phosphoryl transferases, including kinases, may be involved, symptoms of such disease, or the effect of other physiological events mediated by phosphoryl transferases, including kinases. The invention also provides for methods of making the inhibitor compounds and methods for treating diseases in which one or more phosphoryl transferase, including kinase, activities is involved.

Alternatively, the present compounds can also be used in co-therapies with other anti-neoplastic agents, such as other kinase inhibitors including p38 inhibitors and CDK inhibitors, TNF inhibitors, metallomatrix proteases inhibitors (MMP), EGFR inhibitors such as Iressa, KDR inhibitors, COX-2 inhibitors including celecoxib, rofecoxib, parecoxib, valdecoxib, and etoricoxib, NSAID's, SOD mimics or αvβ3 inhibitors.

As yet another specific example, the compounds of the invention and/or compositions thereof may be administered in combination with both ribovirin and an interferon.

EXAMPLES

The following examples are provided by way of illustration only and not by way of limitation. Those of skill in the art will readily recognize a variety of noncritical parameters that could be changed or modified to yield essentially similar results.

The examples are offered for illustrative purposes only, and are not intended to limit the scope of the present invention in any way. Efforts have been made to ensure accuracy with respect to numbers used (e.g., amounts, temperatures, etc.), but some experimental error and deviation should, of course, be allowed for.

Example 1

Synthesis of N2-Chlorocarbonyl-N4-(2,2-dimethyl-3-oxo-4H-5-pyrido[1,4]oxazin-6-yl)-5-fluoro-N2-(3,4,5-trimethoxyphenyl)-2,4-pyrimidinediamine

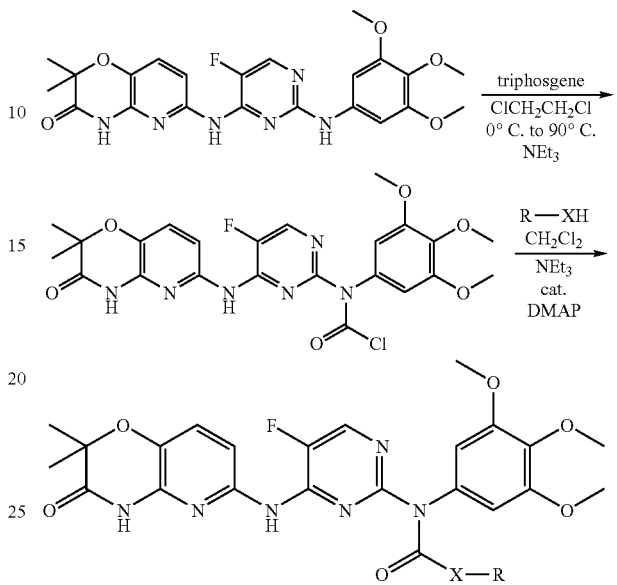

To pale yellow stirring mixture of N4-(2,2-dimethyl-3-oxo-4H-5-pyrido[1,4]oxazin-6-yl)-5-fluoro-N2-(3,4,5-trimethoxyphenyl)-2,4-pyrimidinediamine (2.5 g, 5.31 mmol) and triphosgene (1.67 g, 5.62 mmol) in dicholoroethane (20 mL) at 0°C, NEt$_3$ (1.08 g, 1.5 mL, 10.76 mmol) in dichloroethane (10 mL) was added dropwise under nitrogen atmosphere for 10 min. The orange reaction mixture was allowed to stir for 15 min at 0°C followed by refluxing at 90°C overnight. The heterogeneous tan orange reaction mixture was cooled to room temperature. The reaction mixture was diluted with EtOAc (75 mL). Precipitated white solid formed was filtered. The white solid was collected, treated with water, filtered and dried to provide N2-chlorocarbonyl-N4-(2,2-dimethyl-3-oxo-4H-5-pyrido[1,4]oxazin-6-yl)-5-fluoro-N2-(3,4,5-trimethoxyphenyl)-2,4-pyrimidinediamine (1.75 g, 61%). $^1$H NMR (DMSO-d$_6$): δ 11.08 (s, 1H), 9.97 (s, 1H), 8.44 (d, 1H, J=3.2 Hz), 7.35 (d, 1H, J=8.5 Hz), 7.24 (d, 1H, J=8.5 Hz), 6.77 (s, 1H), 3.72 (s, 6H), 3.66 (s, 3H), 1.40 (s, 6H). LCMS: ret. time: 12.53 min.; purity: 95%; MS (m/e): 534 (MH$^+$).

General Procedure for the Preparation of Carbamates and Thiocarbamates:

N2-chlorocarbonyl-N4-(2,2-dimethyl-3-oxo-4H-5-pyrido[1,4]oxazin-6-yl)-5-fluoro-N2-(3,4,5-trimethoxyphenyl)-2,4-pyrimidinediamine (1 eq) prepared in Example 1 was dissolved in dry CH$_2$Cl$_2$ (4.8 mL/mmol), alcohol (for carbamates) or thiol (for thiocarbamates) (2 eq), NEt$_3$ (7 eq) and DMAP (0.1 eq) were added successively under nitrogen atmosphere at room temperature. Contents were allowed to stir at room temperature and progress of the reaction mixture was monitored by LC/MS. The reaction mixture was concentrated upon consumption of carbamoylchloride. The crude concentrate was treated with aq. NaHCO$_3$ and the resulting solid precipitated was filtered, washed with water, dried and purified by either silica gel column chromatography or preparative HPLC.

Example 2

Synthesis of N4-(2,2-Dimethyl-3-oxo-4H-5-pyrido[1,4]oxazin-6-yl)-5-fluoro-N2-[[2-(morpholin-4-yl)ethoxy]carbonyl]-N2-(3,4,5-trimethoxyphenyl)-2,4-pyrimidinediamine

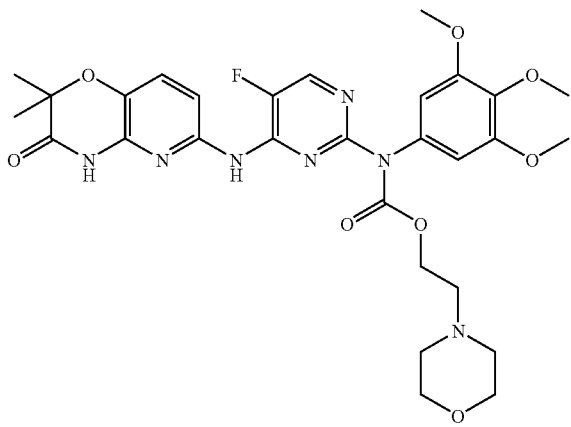

N4-(2,2-Dimethyl-3-oxo-4H-5-pyrido[1,4]oxazin-6-yl)-5-fluoro-N2-[[2-(morpholin-4-yl)ethoxy]carbonyl]-N2-(3,4,5-trimethoxyphenyl)-2,4-pyrimidinediamine was prepared from 4-(2-hydroxyethyl)morpholine and N2-chlorocarbonyl-N4-(2,2-dimethyl-3-oxo-4H-5-pyrido[1,4]oxazin-6-yl)-5-fluoro-N2-(3,4,5-trimethoxyphenyl)-2,4-pyrimidinediamine. The crude solid, obtained after concentration of the reaction mixture followed by treatment with aq. $NaHCO_3$, was purified by $NEt_3$ treated silica gel column chromatography. $^1H$ NMR ($CDCl_3$): δ 10.32 (s, 2H), 8.89 (s, 1H), 8.18 (d, 1H, J=2.9 Hz), 7.49 (d, 1H, J=8.8 Hz), 7.06 (d, 1H, J=8.8 Hz), 6.52 (s, 2H), 4.29 (m, 2H), 3.81 (s, 3H), 3.74 (s, 6H), 3.57 (m, 4H), 2.56 (m, 2H), 2.33 (m, 4H), 1.48 (s, 6H). LCMS: ret. time: 8.30 min.; purity: 92%; MS (m/e): 628 ($MH^+$).

Example 3

Synthesis of 4-(2,2-Dimethyl-3-oxo-4H-5-pyrido[1,4]oxazin-6-yl)-5-fluoro-N2-[[1-methyl-piperidin-2-yl)methoxy]carbonyl]-N2-(3,4,5-trimethoxyphenyl)-2,4-pyrimidinediamine

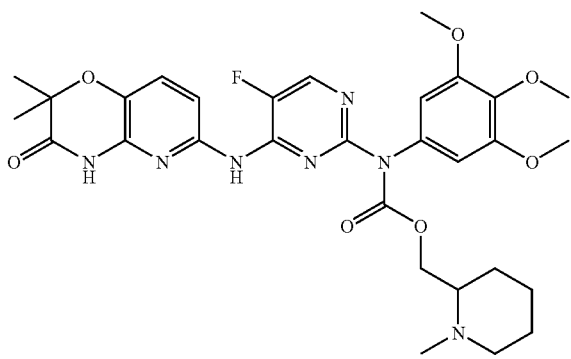

4-(2,2-Dimethyl-3-oxo-4H-5-pyrido[1,4]oxazin-6-yl)-5-fluoro-N2-[[1-methyl-piperidin-2-yl)methoxy]carbonyl]-N2-(3,4,5-trimethoxyphenyl)-2,4-pyrimidinediamine was prepared from N2-chlorocarbonyl-N4-(2,2-dimethyl-3-oxo-4H-5-pyrido[1,4]oxazin-6-yl)-5-fluoro-N2-(3,4,5-trimethoxyphenyl)-2,4-pyrimidinediamine and 1-methyl-2-piperidinemethanol in the similar manner as described in the general procedure. The crude off white solid obtained after the general workup was subjected to HPLC purification. $^1H$ NMR (DMSO-d6): δ 11.03 (s, 1H), 9.67 (s, 1H), 8.33 (d, 1H, J=3.0 Hz), 7.41 (d, 1H, J=8.5 Hz), 7.17 (d, 1H, J=8.5 Hz), 6.56 (s, 2H), 4.10 (d, 2H, J=4.7 Hz), 3.80 (s, 6H), 3.64 (s, 3H), 2.70-2.66 (m, 1H), 2.09 (s, 3H), 1.97-1.92 (m, 2H), 1.58-1.07 (m, 12H). LCMS: ret. time: 8.54 min.; purity: 92%; MS (m/e): 627 ($MH^+$).

Example 4

Synthesis of 2S—N2-[[2-(t-Butoxycarbonyl)amino-3-(1H-indol-3-yl)]propoxycarbonyl]-N4-(2,2-dimethyl-3-oxo-4H-5-pyrido[1,4]oxazin-6-yl)-5-fluoro-N2-(3,4,5-trimethoxyphenyl)-2,4-pyrimidinediamine

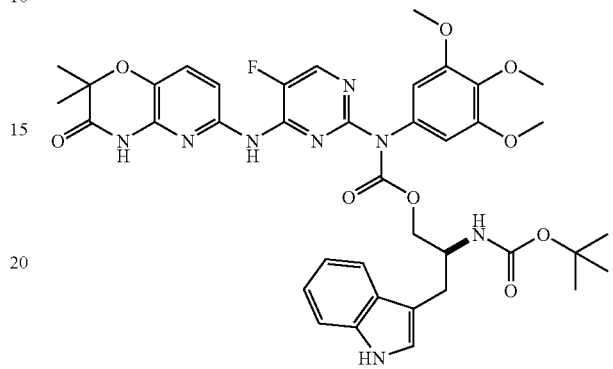

2S—N2-[[2-(t-Butoxycarbonyl)amino-3-(1H-indol-3-yl)]propoxycarbonyl]-N4-(2,2-dimethyl-3-oxo-4H-5-pyrido[1,4]oxazin-6-yl)-5-fluoro-N2-(3,4,5-trimethoxyphenyl)-2,4-pyrimidinediamine was prepared from $N_\alpha$-(t-butoxycarbonyl)-L-tryptophanol and N2-chlorocarbonyl-N4-(2,2-dimethyl-3-oxo-4H-5-pyrido[1,4]oxazin-6-yl)-5-fluoro-N2-(3,4,5-trimethoxyphenyl)-2,4-pyrimidinediamine. The crude white solid collected after the workup was purified by $NEt_3$ treated silica gel column chromatography. $^1H$ NMR (DMSO-d6): δ 11.00 (s, 1H), 10.76 (s, 1H), 9.66 (s, 1H), 8.32 (d, 1H, J=3.2 Hz), 7.36 (d, 1H, J=8.8 Hz), 7.31-7.27 (m, 2H), 7.08 (d, 1H, J=8.5 Hz), 7.03-6.99 (m, 2H), 6.91-6.86 (m, 1H), 6.78 (d, 1H, J=8.2 Hz), 6.65 (s, 2H), 4.12-4.08 (m, 1H), 3.99-3.94 (m, 1H), 3.86-3.82 (m, 1H), 3.69 (s, 6H), 3.63 (s, 3H), 2.74 (m, 2H), 1.38 (s, 6H), 1.29 (s, 9H). LCMS: ret. time: 13.63 min.; purity: 91%; MS (m/e): 787 ($MH^+$).

Example 5

Synthesis of 2S—N2-[[2-Amino-3-(1H-indol-3-yl)]propoxycarbonyl]-N4-(2,2-dimethyl-3-oxo-4H-5-pyrido[1,4]oxazin-6-yl)-5-fluoro-N2-(3,4,5-trimethoxyphenyl)-2,4-pyrimidinediamine

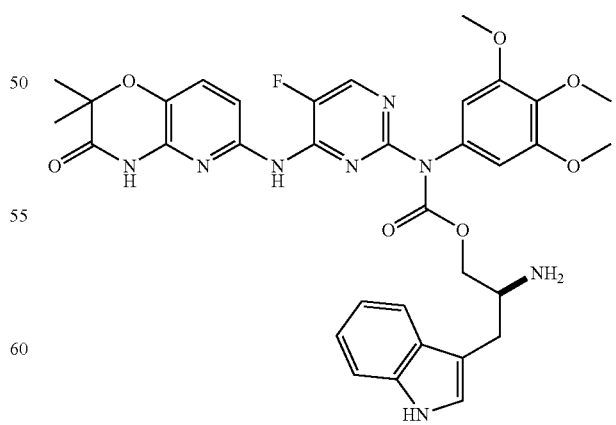

Trifluoracetic acid (0.04 mL, 59 mg, 0.519 mmol) was added to the stirring solution of 2S—N2-[[2-Amino-3-(1H-indol-3-yl)]propoxycarbonyl]-N4-(2,2-dimethyl-3-oxo-4H-5-pyrido[1,4]oxazin-6-yl)-5-fluoro-N2-(3,4,5-trimethoxyphenyl)-2,4-pyrimidinediamine (93 mg, 0.118 mmol) in CH₂Cl₂ (5 mL) at 0°C Progress of the reaction was monitored by LC/MS. Reaction mixture was concentrated after 1 hr of stirring the reaction mixture at 0°C The crude was triturated with anhydrous Et₂O. Ethereal layer was decanted and dried to provide off white solid. The solid obtained was purified by HPLC to give 26 mg (32%) of N2-[[[(2S)-2-amino-3-(1H-indol-3-yl)]propoxy]carbonyl]-N4-(2,2-dimethyl-3-oxo-4H-5-pyrido[1,4]oxazin-6-yl)-5-fluoro-N2-(3,4,5-trimethoxyphenyl)-2,4-pyrimidinediamine as a white solid. LCMS: ret. time: 9.34 min.; purity: 92%; MS (m/e): 687 (MH⁺).

Example 6

Synthesis of N4-(2,2-Dimethyl-3-oxo-4H-5-pyrido[1,4]oxazin-6-yl)-5-fluoro-N2-[2-[4-(3-sulfopropyl)piperizin-1-yl]ethoxycarbonyl]-N2-(3,4,5-trimethoxyphenyl)-2,4-pyrimidinediamine

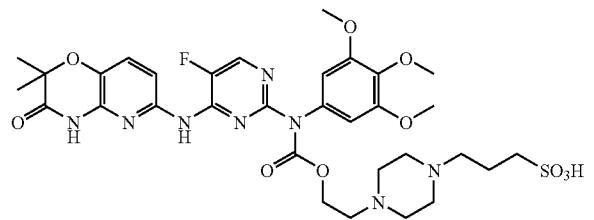

N4-(2,2-Dimethyl-3-oxo-4H-5-pyrido[1,4]oxazin-6-yl)-5-fluoro-N2-[2-[4-(3-sulfopropyl)piperizin-1-yl]ethoxycarbonyl]-N2-(3,4,5-trimethoxyphenyl)-2,4-pyrimidinediamine was prepared in the similar manner as described in the general procedure from N2-chlorocarbonyl-N4-(2,2-dimethyl-3-oxo-4H-5-pyrido[1,4]oxazin-6-yl)-5-fluoro-N2-(3,4,5-trimethoxyphenyl)-2,4-pyrimidinediamine and 4-(2-hydroxyethyl)-piperazinepropanesulfonic acid (EPPS) in CH₃CN. Reaction mixture was concentrated and diluted with water. The solid precipitated was filtered, dried and purified by preparative HPLC. ¹H NMR (DMSO-d6): δ 11.03 (s, 1H), 9.68 (s, 1H), 8.35 (d, 1H, J=3.2 Hz), 7.34 (d, 1H, J=8.8 Hz), 7.15 (d, 1H, J=8.8 Hz), 6.57 (s, 2H), 4.19 (m, 2H), 3.69 (s, 6H), 3.65 (s, 3H), 3.30-2.86 (m, 8H), 2.57-2.52 (m, 4H), 2.37-2.26 (m, 2H), 1.93-1.91 (m, 2H), 1.39 (s, 6H). LCMS: ret. time: 8.32 min.; purity: 98%; MS (m/e): 749 (MH⁺).

Example 7

Synthesis of N2-[2-(Dimethylamino)ethoxycarbonyl]-N4-(2,2-dimethyl-3-oxo-4H-5-pyrido[1,4]oxazin-6-yl)-5-fluoro-N2-(3,4,5-trimethoxyphenyl)-2,4-pyrimidinediamine

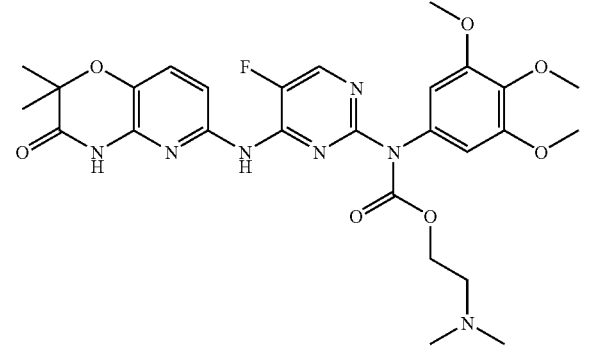

N2-[2-(Dimethylamino)ethoxycarbonyl]-N4-(2,2-dimethyl-3-oxo-4H-5-pyrido[1,4]oxazin-6-yl)-5-fluoro-N2-(3,4,5-trimethoxyphenyl)-2,4-pyrimidinediamine was prepared from N2-chlorocarbonyl-N4-(2,2-dimethyl-3-oxo-4H-5-pyrido[1,4]oxazin-6-yl)-5-fluoro-N2-(3,4,5-trimethoxyphenyl)-2,4-pyrimidinediamine and N,N-dimethylethanolamine. The crude solid obtained was purified by preparative HPLC. ¹H NMR (DMSO-d6): δ 11.04 (s, 1H), 9.68 (s, 1H), 8.33 (d, 1H, J=3.5 Hz), 7.39 (d, 1H, J=8.5 Hz), 7.16 (d, 1H, J=8.5 Hz), 6.54 (s, 2H), 4.17 (t, 2H, J=5.8 Hz), 3.68 (s., 6H), 3.64 (s, 3H), 2.45 (t, 2H, J=5.8 Hz), 2.08 (s, 6H), 1.39 (s, 6H). LCMS: ret. time: 8.87 min.; purity: 99%; MS (m/e): 586 (MH⁺).

Example 8

Synthesis of 1S—N2-[[-1-(t-Butoxycarbonyl)-2-methylpropyl]aminocarbonyl]-N4-(2,2-dimethyl-3-oxo-4H-5-pyrido[1,4]oxazin-6-yl)-5-fluoro-N2-(3,4,5-trimethoxyphenyl)-2,4-pyrimidinediamine

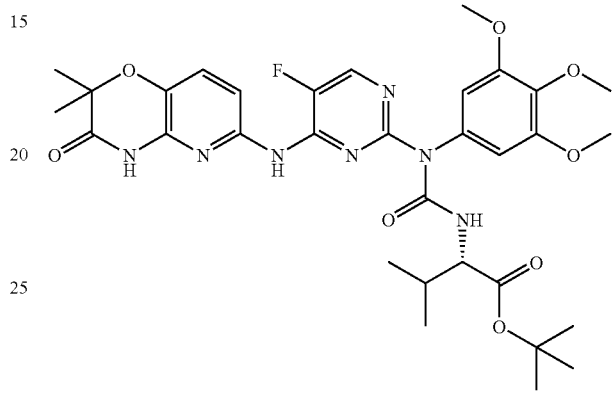

1S—N2-[[-1-(t-Butoxycarbonyl)-2-methylpropyl]aminocarbonyl]-N4-(2,2-dimethyl-3-oxo-4H-5-pyrido[1,4]oxazin-6-yl)-5-fluoro-N2-(3,4,5-trimethoxyphenyl)-2,4-pyrimidinediamine was prepared from N2-chlorocarbonyl-N4-(2,2-dimethyl-3-oxo-4H-5-pyrido[1,4]oxazin-6-yl)-5-fluoro-N2-(3,4,5-trimethoxyphenyl)-2,4-pyrimidinediamine and L-valine t-butyl ester hydrochloride in the similar manner as described in the general procedure. ¹H NMR (DMSO-d6): δ 10.97 (s, 1H), 10.45 (d, 1H, J=7.6 Hz), 8.35 (d, 1H, J=3.5 Hz), 6.75 (d, 1H, J=8.8 Hz), 6.71 (d, 1H, J=8.8 Hz), 6.52 (s, 2H), 4.15 (dd, 1H, J=4.7 and 6.7 Hz), 3.71 (s, 3H), 3.66 (s, 6H), 2.15 (m, 1H), 1.42 (s, 9H), 1.38 (s, 6H), 0.93 (dd, 6H, J=1.7 and 6.7 Hz). LCMS: ret. time: 14.87 min.; purity: 93%; MS (m/e): 670 (MH⁺).

Example 9

Synthesis of N2-[2-(Carboxymethyl)aminocarbonyl]-N4-(2,2-dimethyl-3-oxo-4H-5-pyrido[1,4]oxazin-6-yl)-5-fluoro-N2-(3,4,5-trimethoxyphenyl)-2,4-pyrimidinediamine

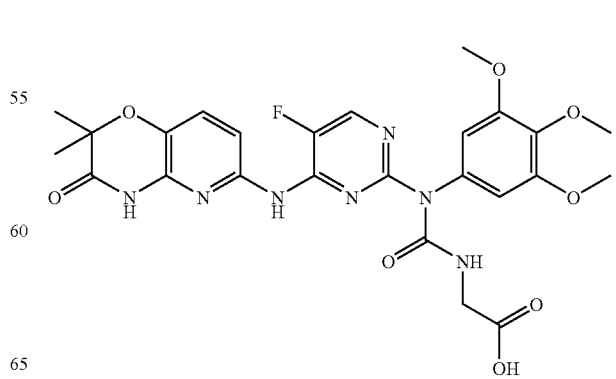

N2-[2-(Carboxymethyl)aminocarbonyl]-N4-(2,2-dimethyl-3-oxo-4H-5-pyrido[1,4]oxazin-6-yl)-5-fluoro-N2-(3,4,5-trimethoxyphenyl)-2,4-pyrimidinediamine was prepared in the similar as described in the general procedure from glycine and N2-chlorocarbonyl-N4-(2,2-dimethyl-3-oxo-4H-5-pyrido[1,4]oxazin-6-yl)-5-fluoro-N2-(3,4,5-trimethoxyphenyl)-2,4-pyrimidinediamine. The crude concentrated reaction mixture was treated with 1N aq. HCl. The solid precipitated was dried and purified by preparative HPLC. $^1$H NMR (DMSO-d6): δ 10.99 (s, 1H), 10.06 (t, 1H, J=5.0 Hz), 8.26 (d, 1H, J=3.8 Hz), 6.78 (app s, 2H), 6.51 (s, 2H), 3.85 (d, 2H, J=5.0 Hz), 3.71 (s, 3H), 3.67 (s, 6H), 1.37 (s, 6H). LCMS: ret. time: 9.74 min.; purity: 97%; MS (m/e): 572 (MH$^+$).

Example 10

Synthesis of (+/−)-N4-(2,2-Dimethyl-3-oxo-4H-5-pyrido[1,4]oxazin-6-yl)-5-fluoro-N2-[[1(1-pyridinium)ethoxy)carbonyl]]-N2-(3,4,5-trimethoxyphenyl)-2,4-pyrimidinediamine iodide salt The intermediate (+/−)-N2-(1-Chloroethoxycarbonyl)-N4-(2,2-dimethyl-3-oxo-4H-5-pyrido[1,4]oxazin-6-yl)-5-fluoro-N2-(3,4,5-trimethoxyphenyl)-2,4-pyrimidinediamine was first synthesized. To a stirring mixture of N4-(2,2-dimethyl-3-oxo-4H-5-pyrido[1,4]oxazin-6-yl)-5-fluoro-N2-(3,4,5-trimethoxyphenyl)-2,4-pyrimidinediamine (250 mg, 0.53 mmol) and i-Pr$_2$NEt (0.14 mL, 102 mg, 0.78 mmol) in dicholoroethane (10 mL) at −78°C, 1-chloroethyl chloroformate (0.07 mL, 90 mg, 0.638 mmol) was added dropwise under nitrogen atmosphere over 5 min. After 1 h, the reaction mixture was diluted with EtOAc (10 mL) at −78°C. Reaction mixture was allowed to warm to room temperature while stirring. Solid precipitated from pale brown transparent reaction mixture after stirring the contents at room temperature for 1 h. Reaction mixture was concentrated and diluted with water (15 mL). The precipitated solid was filtered and dried to provide (+/−)-N2-(1-chloroethoxycarbonyl)-N4-(2,2-dimethyl-3-oxo-4H-5-pyrido[1,4]oxazin-6-yl)-5-fluoro-N2-(3,4,5-trimethoxyphenyl)-2,4-pyrimidinediamine (250 mg, 81%). $^1$H NMR (DMSO-d$_6$): δ 11.04 (s, 1H), 9.78 (s, 1H), 8.37 (d, 1H, J=3.2 Hz), 7.39 (d, 1H, J=8.5 Hz), 7.17 (d, 1H,

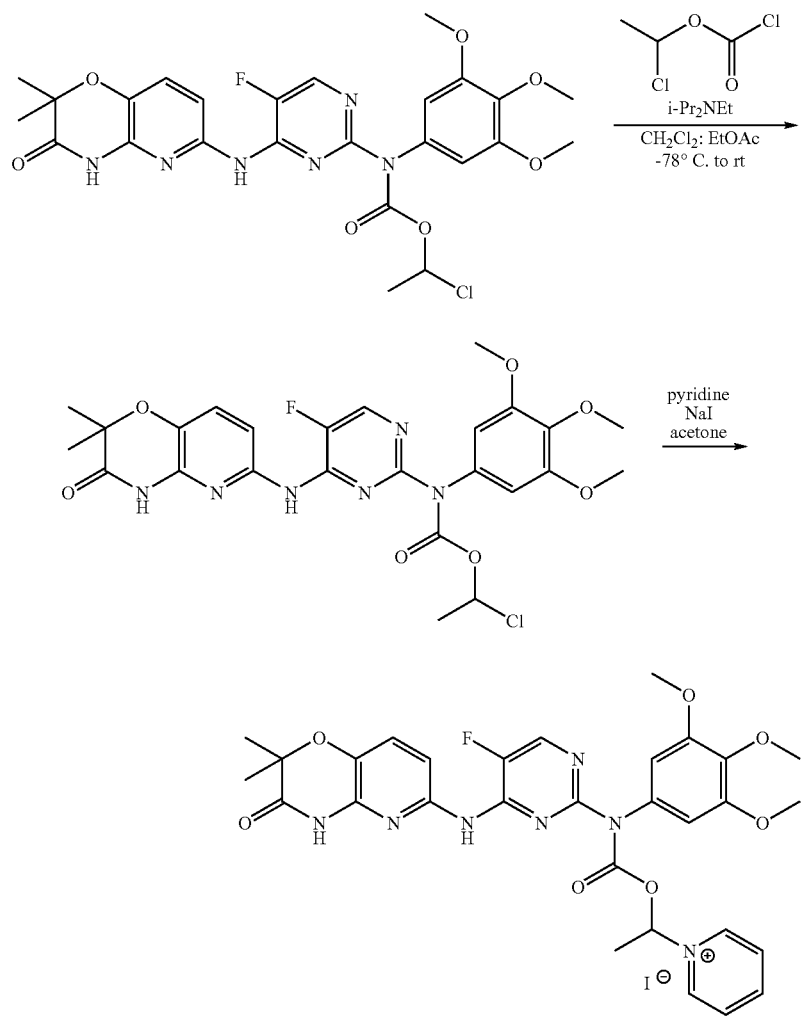

J=8.5 Hz), 6.64 (qt, 1H, J=5.7 Hz), 6.57 (s, 2H), 3.69 (s, 6H), 3.65 (s, 3H), 1.65 (d, 3H, J=5.7 Hz), 1.39 (s, 6H). LCMS: ret. time: 10.35 min.; purity: 95%; MS (m/e): 578 (MH$^+$).

Synthesis of (+/−)-N4-(2,2-Dimethyl-3-oxo-4H-5-pyrido[1,4]oxazin-6-yl)-5-fluoro-N2-[[1(1-pyridinium)ethoxy)carbonyl]]-N2-(3,4,5-trimethoxyphenyl)-2,4-pyrimidinediamine iodide salt (+/−)-N2-(1-Chloroethoxycarbonyl)-N4-(2,2-dimethyl-3-oxo-4H-5-pyrido[1,4]oxazin-6-yl)-5-fluoro-N2-(3,4,5-trimethoxyphenyl)-2,4-pyrimidinediamine (50 mg, 0.086 mmol), pyridine (34 mg, 0.43 mmol) and NaI (129 mg, 0.86 mmol) in acetone were stirred at room temperature for 24 h. The reaction mixture was concentrated, diluted with water (5 mL) and EtOAc (5 mL). The precipitate (pale brown) was filtered and dried to provide the desired product, (+/−)-N4-(2,2-dimethyl-3-oxo-4H-5-pyrido[1,4]oxazin-6-yl)-5-fluoro-N2-[[1(1-pyridinium)ethoxy)carbonyl]]-N2-(3,4,5-trimethoxyphenyl)-2,4-pyrimidinediamine iodide salt. LCMS: ret. time: 8.82 min.; purity: 90%; MS (m/e): 620 (M$^+$). The remaining impurity was characterized as N4-(2,2-dimethyl-3-oxo-4H-5-pyrido[1,4]oxazin-6-yl)-5-fluoro-N2-(3,4,5-trimethoxyphenyl)-2,4-pyrimidinediamine.

Example 11

Pharmacokinetics and Metabolism of the Compounds

Compounds were administered to rats orally at a dose of 4-5 mg/kg using PEG-400 as a vehicle. Selected compounds were also administered as an IV bolus at a dose of 1 mg/kg. Plasma samples were obtained from either the portal or jugular veins and analyzed by LC/MS/MS for both the parent pyrimidine-2,4-diamine and the prodrug compounds synthesized in the examples above. Bioavailability was calculated using the AUC of pyrimidine-2,4-diamine in jugular vein samples and the AUC of an IV bolus dose of pyrimidine-2,4-diamine. For selected compounds, portal vein samples were evaluated for both prodrug and pyrimidine-2,4-diamine and the information was used to determine the percent absorption of the orally administered dose. Results from the in vivo evaluation of the compounds in rats are shown in Table 1.

Many of the prodrugs evaluated orally in rats show the presence of pyrimidine-2,4-diamine in systemic circulation as shown in Table 1 (% F and Cmax). Thus, the in vivo studies demonstrate that the prodrug moiety is enzymatically cleaved in vivo and results in systemic circulation of pyrimidine-2,4-diamine parent molecule.

Selected compounds were incubated in rat and human hepatic microsomes (with and without NADPH) and analyzed by LC/MS/MS for both the prodrug and pyrimidine-2,4-diamine. The results of the compounds evaluated in vitro in hepatic microsome studies are listed in Table 2.

TABLE 2

Metabolic stability of prodrugs in hepatic microsomes.

| | | | Results | |
|---|---|---|---|---|
| Compound disclosed in: | System | $T_{1/2}$[4] | CYP450 dependent[5]? | Pyrimidine-2,4-diamine produced? |
| Example 2 | Rat and Human microsomes | <5/<5 | Y | Y |
| Example 3 | Rat and Human microsomes | <5/<5 | Y | Y |
| Example 8 | Rat and Human microsomes | 35/10 | Y | Y |

[4]Half-life of prodrug in the presence of NASDPH
[5]Determined by incubating compounds in microsomes in the absence of NADPH. All of the compounds in the list were stable in the absence of NADPH.

Studies were conducted in microsomes to determine whether the prodrug moieties could be hydrolyzed by CYP450 enzymes. The results from the use of compounds prepared in Examples 2, 3, and 8 provide clear evidence for P450 dependent cleavage of the prodrug moiety. Since microsomes lack many of the cytosolic enzymes present in rat and human liver, failure to detect pyrimidine-2,4-diamine in microsomal incubations does not preclude conversion in vivo.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to one

TABLE 1

Summary of the pharmacokinetics of the compounds in sprague-dawley rats.

| Compound disclosed in: | Study # | Mode of administration | % F[1] | Cmax of pyrimidine-2,4-diamine[2] | Clearance rate of prodrug, ml/min/kg | % of prodrug absorbed[3] |
|---|---|---|---|---|---|---|
| Example 2 | VO40197 | IV and PO | 3.1 | 41.6 | 72 | 20 |
| Example 3 | VO40219 | PO | 3 | 26.3 | — | — |
| Example 5 | VO40219 | PO | 27 | 237 | — | — |
| Example 6 | VO40219 | PO | 0 | 0 | — | — |
| Example 9 | VO40219 | PO | 3 | 26.3 | — | — |

[1]% F calculated based on pyrimidine-2,4-diamine concentrations in jugular vein samples.
[2]Highest observed concentration of pyrimidine-2,4-diamine in plasma following a 4 mg/kg oral dose or prodrug
[3]Calculated based on the following formula: % absorption = (AUC of prodrug in portal vein following oral administration/AUC or prodrug in jugular vein following IV administration) * (IV dose/e) * 100

The invention claimed is:

1. A compound of formula (I)

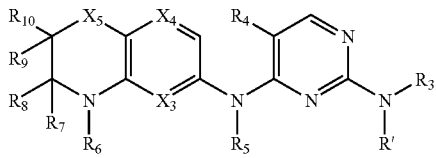

I or a salt or N-oxide thereof;
wherein $R_3$ is aryl or heteroaryl, each optionally substituted; $X_3$ and $X_4$ are
independently CH or N;
$X_5$ is selected from the group consisting of $CR_{12}R_{13}$, O, S, SO, $SO_2$, and $NR_{14}$ wherein $R_{12}$ and $R_{13}$ are independently selected from H, OH, and lower alkyl, or together form an oxo group;
$R_4$ is selected from the group consisting of OH, acyl, formyl, sulfonyl, alkoxy, carboxylate, haloalkyl, halogen, cyano, nitro, trifluoromethoxy, difluoromethoxy, and fluoromethoxy;
R', $R_5$, $R_6$ and $R_{14}$ are independently selected from the group consisting of H, lower alkyl, $R_p$, cycloalkyl and aryl, and wherein at least one of R', $R_5$, $R_6$ and $R_{14}$ is $R_p$ linked via —C(O)O—, —C(S)O—, -C(O)S—, —C(S)S—, —C(O)NH— or —C(S)NH—;
$R_p$ is —$(CR_1R_2)_n$—R;
R is selected from the group consisting of acetate, amino, dialkylamino, —C(O)OH, alkyl, allyl, cycloalkyl, cycloheteroalkyl, aryl, heteroaryl, phenylalkaryl and heteroarylalkyl, each of which is optionally substituted;
$R_1$ and $R_2$ are each independently selected from the group consisting of H, OH, —$OR_{11}$, $NR_{15}R_{15}$, halo, lower alkyl, C(O)O-alkyl, —C(O)OH, —OP(=O)$(OR_{11})_2$, —OC(=O) $OR_{11}$, —OC(=O)$R_{11}$, cycloalkyl, aryl, and heteroaryl or together form an oxo, wherein each $R_{15}$ is independently selected from the group consisting of H, lower alkyl, prenyl, allyl, —C(O))-alkyl, cycloalkyl, aryl, heteroaryl, alkaryl and alkheteroaryl, or two of $R_{15}$ combine to form an optionally substituted cycloheteroalkyl;
each $R_{11}$ is independently H or lower alkyl;
n is an integer from 0 to 10;
$R_7$ and $R_8$ are independently selected from the group consisting of H, halogen, lower alkyl, cycloalkyl, aryl, and heteroaryl; and
$R_9$ and $R_{10}$ are independently selected from the group consisting of H, halogen, —OH, -alkoxy, lower alkyl, cycloalkyl, aryl, and heteroaryl wherein $R_7$ and $R_8$, or $R_9$ and $R_{10}$ together form an oxo group, and wherein $R_9$ or $R_{10}$ are not —OH or alkoxy when $X_5$ is $NR_{14}$.

2. A compound of formula (II)

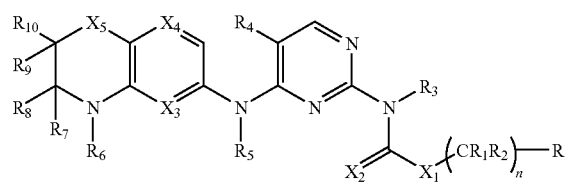

II or a salt and/or N-oxide thereof,
wherein $X_1$ is selected from the group consisting of O, S, and $NR_{11}$ wherein $R_{11}$ is H or lower alkyl;
$X_2$ is O or S;
$X_3$ and $X_4$ are independently CH or N;
$X_5$ is selected from the group consisting of $CR_{12}R_{13}$, O, S, SO, $SO_2$, and $NR_{14}$ wherein $R_{12}$ and $R_{13}$ are independently selected from H, OH, and lower alkyl, or together form an oxo group, and $R_{14}$ is H or lower alkyl;
R is selected from the group consisting of acetate, amino, dialkylamino, —C(O)OH, alkyl, allyl, cycloalkyl, cycloheteroalkyl, aryl, heteroaryl, phenylalkaryl and heteroarylalkyl, each of which is optionally substituted;
$R_1$ and $R_2$ are each independently selected from the group consisting of H, OH, —$OR_{11}$, $NR_{15}R_{15}$, halo, lower alkyl, —C(O)O-alkyl, —C(O)OH, —OP(=O)$(OR_{11})_2$, —OC(=O) $OR_{11}$, —OC(=O)$R_{11}$, cycloalkyl, aryl, and heteroaryl or together form an oxo, wherein each $R_{15}$ is independently selected from the group consisting of H, lower alkyl, prenyl, allyl —C(O)O-alkyl, cycloalkyl, aryl, heteroaryl, alkaryl and alkheteroaryl, or two of $R_{15}$ combine to form an optionally substituted cycloheteroalkyl;
$R_3$ is aryl or heteroaryl, each optionally substituted;
$R_4$ is selected from the group consisting of OH, acyl, formyl, sulfonyl, alkoxy, carboxylate, haloalkyl, halogen, cyano, nitro, trifluoromethoxy, difluoromethoxy, and fluoromethoxy;
$R_5$ and $R_6$ are independently selected from H, lower alkyl, cycloalkyl or aryl;
$R_7$, $R_8$, $R_9$, and $R_{10}$ are independently selected from the group consisting of H, OH, halogen, lower alkyl, cycloalkyl, aryl, and heteroaryl, or wherein $R_7$ and $R_8$ or $R_9$ and $R_{10}$ together form an oxo group; and
n is an integer from 0 to 10.

3. The compound of claim 2, wherein $X_1$ is 0.
4. The compound of claim 3, wherein $X_2$ is 0.
5. The compound of claim 2, wherein $R_3$ is optionally substituted aryl.
6. The compound of claim 5, wherein aryl is alkoxyphenyl, dialkoxyphenyl, or trialkoxyphenyl.
7. The compound of claim 6, wherein trialkoxyphenyl is trimethoxyphenyl.
8. The compound of claim 2, wherein $R_4$ is OH, halogen, cyano, nitro, trifluoromethyl, difluoromethyl, fluoromethyl, trifluoromethoxy, difluoromethoxy, or fluoromethoxy.
9. The compound of claim 8, wherein $R_4$ is F.
10. The compound of claim 2, wherein $R_5$ and $R_6$ are H.
11. The compound of claim 2, wherein $X_4$ is CH.
12. The compound of claim 2, wherein $X_4$ is N.
13. The compound of claim 2, wherein $X_5$ is $CH_2$ or O.
14. The compound of claim 2, wherein $R_7$ and $R_8$ are H or together form the oxo group.
15. The compound of claim 2, wherein $R_9$ and $R_{10}$ are methyl.
16. The compound of claim 2, wherein R is cycloheteroalkyl.
17. The compound of claim 16, wherein R is substituted or unsubstituted morpholine, or substituted or unsubstituted pyrrolidine.
18. The compound of claim 2, wherein R is heteroaryl.
19. The compound of claim 18, wherein heteroaryl is substituted or unsubstituted indole.
20. The compound of claim 2, wherein R is selected from the group consisting of acetate, amino, and dialkylamino.
21. The compound of claim 2, wherein n is 1, 2, or 3.
22. The compound of claim 1, wherein $X_1$ is $NR_{11}$.
23. The compound of claim 22, wherein $X_2$ is O.
24. The compound of claim 22, wherein $X_2$ is S.
25. The compound of claim 1, wherein $X_1$ is S.

26. The compound of claim 25, wherein $X_2$ is O.

27. A compound of formula (III):

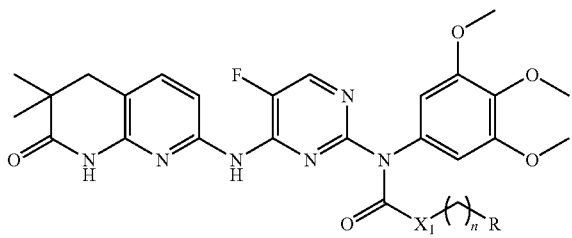

III or a salt and or N-oxide thereof;
wherein R is selected from the group consisting of acetate, amino, dialkylamino, —C(O)OH, straight or branched, saturated or unsaturated alkyl, allyl, cycloalkyl, cycloheteroalkyl, aryl, and heteroaryl, each of which is optionally substituted;

$X_1$ is O or $NR_{11}$;

$R_{11}$ is H or lower alkyl; and n is and integer between 0 and 10.

28. The compound of claim 27, wherein R is morpholine.

29. The compound of claim 27, wherein R is 1-methylpiperidine.

30. The compound of claim 27, wherein R is piperazine or 3-piperazinepropane sulfonate.

31. The compound of claim 27, wherein R is dimethylamine.

32. The compound of claim 27, wherein R is tryptamine or N-tert-butylaceyltryptamine.

33. The compound of claim 27, wherein n is 0, 1, 2, or 3.

34. A method for of treating breast cancer, the method comprising:
administering to a subject an effective amount of a compound of claim 1 or a acceptable salt or N-oxide thereof and pharmaceutically-acceptable carrier or diluent.

35. The method of claim 34, wherein the subject is a domestic animal.

36. The method of claim 34, wherein the subject is a human.

* * * * *

UNITED STATES PATENT AND TRADEMARK OFFICE
CERTIFICATE OF CORRECTION

PATENT NO.       : 7,713,987 B2
APPLICATION NO.  : 11/295752
DATED            : May 11, 2010
INVENTOR(S)      : Somasekhar Bhamidipati and Rajinder Singh It is certified that error appears in the above-identified patent and that said Letters Patent is hereby corrected as shown below:

At column 17, lines 10-20, please delete the chemical structure labeled as formula (III), and replace it with the following:

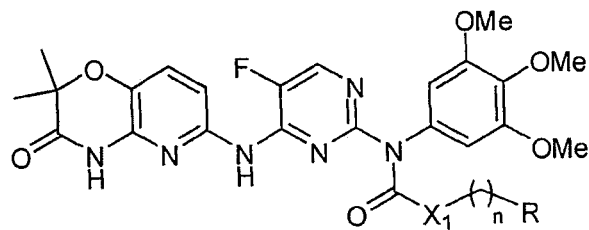

At column 45, lines 5-15, please delete the chemical structure labeled as formula (III), and replace it with the following:

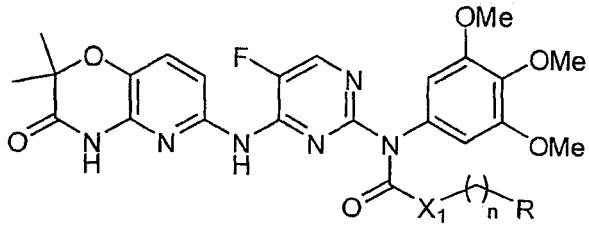

Signed and Sealed this
Thirteenth Day of September, 2011

David J. Kappos
*Director of the United States Patent and Trademark Office*